US010272416B2

(12) United States Patent
Velasquez et al.

(10) Patent No.: US 10,272,416 B2
(45) Date of Patent: Apr. 30, 2019

(54) CATALYSTS FOR THE DEHYDRATION OF HYDROXYPROPIONIC ACID AND ITS DERIVATIVES

(71) Applicant: The Procter & Gamble Company, Cincinnati, OH (US)

(72) Inventors: Juan Esteban Velasquez, Cincinnati, OH (US); Dimitris Ioannis Collias, Mason, OH (US); Jane Ellen Godlewski, Loveland, OH (US); Fred Christian Wireko, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/861,728

(22) Filed: Jan. 4, 2018

(65) Prior Publication Data
US 2018/0126363 A1 May 10, 2018

Related U.S. Application Data

(62) Division of application No. 15/249,743, filed on Aug. 29, 2016, now Pat. No. 9,889,435.
(Continued)

(51) Int. Cl.
B01J 27/16 (2006.01)
B01J 27/18 (2006.01)
B01J 27/186 (2006.01)
B01J 27/188 (2006.01)
B01J 27/195 (2006.01)
C07C 51/377 (2006.01)
B01J 37/04 (2006.01)
B01J 37/08 (2006.01)
(Continued)

(52) U.S. Cl.
CPC .......... *B01J 27/1806* (2013.01); *B01J 23/20* (2013.01); *B01J 27/055* (2013.01); *B01J 35/023* (2013.01); *B01J 37/0036* (2013.01); *B01J 37/04* (2013.01); *B01J 37/08* (2013.01); *C07C 51/377* (2013.01); *H05K 999/99* (2013.01)

(58) Field of Classification Search
CPC ........ B01J 27/16; B01J 27/18; B01J 27/1806; B01J 27/1811; B01J 27/1813; B01J 27/186; B01J 27/188; B01J 27/195; B01J 23/20; B01J 27/055; B01J 35/023; B01J 37/0036; B01J 37/04; B01J 37/08; C07C 51/377
USPC .................................. 502/208–214
See application file for complete search history.

(56) References Cited

U.S. PATENT DOCUMENTS 2,859,240 A 11/1958 Holmen
3,781,222 A * 12/1973 Weisang et al. ..... B01J 27/1806
502/208
(Continued)

OTHER PUBLICATIONS

International Search Report and Written Opinion dated Dec. 6, 2016.
(Continued)

Primary Examiner — Patricia L. Hailey
(74) Attorney, Agent, or Firm — Jason J Camp; James T Fondriest

(57) ABSTRACT

Hydroxypropionic acid, hydroxypropionic acid derivatives, or mixtures thereof are dehydrated using a catalyst and a method to produce bio-acrylic acid, acrylic acid derivatives, or mixtures thereof. A method to produce the dehydration catalyst is also provided.

28 Claims, 1 Drawing Sheet

Related U.S. Application Data

(60) Provisional application No. 62/211,012, filed on Aug. 28, 2015.

(51) Int. Cl.
  B01J 23/20 (2006.01)
  B01J 27/055 (2006.01)
  B01J 35/02 (2006.01)
  B01J 37/00 (2006.01)

(56) References Cited

U.S. PATENT DOCUMENTS

| | | | |
|---|---|---|---|
| 4,695,661 A * | 9/1987 | Homann | B01J 27/1806 502/208 |
| 4,729,978 A * | 3/1988 | Sawicki | B01J 27/1806 502/174 |
| 5,071,754 A | 12/1991 | Walkup et al. | |
| 7,683,220 B2 * | 3/2010 | Matsunami | B01J 27/16 568/485 |
| 9,611,208 B2 * | 4/2017 | Velasquez | C07C 51/377 |
| 9,796,651 B2 * | 10/2017 | Fauconet | C07C 67/08 |
| 2013/0043384 A1 * | 2/2013 | Matsumoto | C08F 220/06 250/282 |
| 2013/0273384 A1 | 10/2013 | Godlewski et al. | |
| 2013/0274516 A1 * | 10/2013 | Velasquez | B01J 27/1806 562/599 |
| 2013/0274517 A1 | 10/2013 | Godlewski et al. | |
| 2017/0056862 A1 * | 3/2017 | Velasquez | B01J 27/1806 |
| 2017/0057900 A1 * | 3/2017 | Velasquez | C07C 51/377 |
| 2017/0057901 A1 * | 3/2017 | Velasquez | B01J 27/1806 |

OTHER PUBLICATIONS

All Office Actions for U.S. Appl. No. 15/249,743, filed Aug. 29, 2016.

\* cited by examiner

CATALYSTS FOR THE DEHYDRATION OF HYDROXYPROPIONIC ACID AND ITS DERIVATIVES

FIELD OF THE INVENTION

The present invention generally relates to dehydration catalysts useful for the conversion of hydroxypropionic acid, hydroxypropionic acid derivatives, or mixtures thereof to acrylic acid, acrylic acid derivatives, or mixtures thereof. The invention also relates to methods of making such dehydration catalysts.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers (SAP), which are used in disposable absorbent articles, comprising diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 (5$^{th}$ Ed., John Wiley & Sons, Inc., 2004). As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 80 years to make bio-based acrylic acid, acrylic acid derivatives, or mixtures thereof from non-petroleum sources, such as lactic acid (also known as 2-hydroxypropionic acid), lactic acid derivatives (e.g. alkyl 2-acetoxy-propionate and 2-acetoxy propionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar (≥90% of theoretical yield, or equivalently, ≥0.9 g of lactic acid per g of sugar). Furthermore, commercial lactic acid purity and economics could favor producing acrylic acid at a cost competitive to petroleum-based acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts, phosphate salts, mixtures of sulfate and phosphate salts, bases, zeolites or modified zeolites, metal oxides or modified metal oxides, and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as propionic acid, CO, and $CO_2$. Omission of the base treatment caused increased amounts of the side products. Another example is Hong et al., Appl. Catal. A: General 396:194-200 (2011), who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as Gunter et al., J. Catalysis 148:252-260 (1994); and Tam et al., Ind. Eng. Chem. Res. 38:3873-3877 (1999). The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested in gas phase reactions with low partial pressures of water, as commonly suggested in the art for dehydration reactions. Finally, the group suggested that the acrylic acid yield is increased (and the by-product yields are decreased) when the surface area of the silica support is low, the reaction temperature is high, the reaction pressure is low, and the residence time of the reactants in the catalyst bed is short.

Finally, the Chinese patent application 200910054519.7 discloses the use of ZSM-5 molecular sieves modified with aqueous alkali (such as $NH_3$, NaOH, and $Na_2CO_3$) or a phosphoric acid salt (such as $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70% at short residence times; 2) low selectivities of acrylic acid, acrylic acid derivatives, or mixtures thereof, i.e., significant amounts of undesired side products, such as acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions. Aside from depositing on the catalysts, these side products, even when present in only small amounts, impose additional costs in processing acrylic acid (when present in the reaction product effluent) towards the manufacture of SAP, for example. These deficiencies of the prior art processes and catalysts render them commercially non-viable.

Accordingly, there is a need for catalysts, methods of making the catalysts, and processes for the dehydration of hydroxypropionic acid, hydroxypropionic acid derivatives, or mixtures thereof to acrylic acid, acrylic acid derivatives, or mixtures thereof, with high yield and selectivity toward acrylic acid, in an efficient manner (i.e. short residence times), and with suitable catalyst longevity.

SUMMARY OF THE INVENTION

In one embodiment of the present invention, a dehydration catalyst is provided. The dehydration catalyst comprises:
(a) one or more amorphous phosphate salts consisting essentially of: i) one or more monovalent cations, and ii) one or more phosphate anions selected from the group represented by empirical formula (I):

$$[H_{2(1-x)}PO_{(4-x)}]^- \qquad (I);$$

wherein x is any real number equal to or greater than 0 and equal to or less than 1; wherein said one or more amorphous phosphate salts are neutrally charged;
(b) one or more crystalline phosphate salts consisting essentially of: i) one or more polyvalent cations, and ii) one or more phosphate anions selected from the group represented by molecular formula (II):

$$[H_{(f-2g-h)}P_fO_{(4f-g)}]^{(2f+h)-} \qquad (II);$$

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and
(c) one or more non-phosphate salts consisting essentially of: i) one or more polyvalent cations, and ii) one or more non-phosphate anions selected from the group represented by molecular formulae (III) and (IV):

$$[H_{(a-2b)}S_cO_{(4c-b)}]^{(2c-a)-} \qquad (III)$$

$$[Ta_{2d}O_{(5d+e)}]^{2e-} \qquad (IV);$$

wherein a and b are positive integers or zero; wherein c, d, and e are positive integers; wherein (a−2b) is equal to or greater than zero; wherein (2c−a) is greater than zero; wherein said one or more non-phosphate salts are neutrally charged;
and wherein said one or more crystalline phosphate salts and said one or more non-phosphate salts are substantially chemically inert to said one or more amorphous phosphate salts.

In another embodiment of the present invention, a method of preparing a dehydration catalyst is provided. The method comprises contacting:
(a) a dehydration catalyst precursor mixture comprising: one or more amorphous phosphate salt precursors, one or more crystalline phosphate salts, and one or more non-phosphate salts; wherein said one or more crystalline phosphate salts and said one or more non-phosphate salts are substantially chemically inert to said one or more amorphous phosphate salt precursors;
(b) wherein said one or more amorphous phosphate salt precursors consist essentially of: i) one or more monovalent cations, and ii) one or more phosphate anions selected from the group represented by molecular formulae (V) and (VI):

$$[H_2P_yO_{(3y+1)}]^{p-} \qquad (V)$$

$$[PO_3]_z^{z-} \qquad (VI);$$

wherein y is any integer number equal to or greater than 1 and z is any integer number equal to or greater than 3; wherein said one or more amorphous phosphate salt precursors are neutrally charged;
wherein said one or more crystalline phosphate salts consists essentially of: i) one or more polyvalent cations, and ii) one or more phosphate anions selected from the group represented by molecular formula (II):

$$[H_{(f-2g-h)}P_fO_{(4f-g)}]^{(2f+h)-} \qquad (II);$$

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and
wherein said one or more non-phosphate salts consist essentially of: i) one or more polyvalent cations, and ii) one or more non-phosphate anions selected from the group represented by molecular formulae (III) and (IV):

$$[H_{(a-2b)}S_cO_{(4c-b)}]^{(2c-a)-} \qquad (III)$$

$$[Ta_{2d}O_{(5d+e)}]^{2e-} \qquad (IV);$$

wherein a and b are positive integers or zero; wherein c, d, and e are positive integers; wherein (a−2b) is equal to or greater than zero; wherein (2c−a) is greater than zero; wherein said one or more non-phosphate salts are neutrally charged; with
b) a gas mixture comprising water vapor;
wherein the water partial pressure in said gas mixture is equal to or greater than the water partial pressure at the triple point of at least one of said one or more amorphous phosphate salt precursors; wherein said contacting step between said dehydration catalyst precursor mixture and said gas mixture is performed at a temperature equal to or greater than the temperature at the triple point of at least one of said one or more amorphous phosphate salt precursors; and wherein one or more amorphous phosphate salts are produced as a result of said one or more amorphous phosphate salt precursors being contacted with said water vapor.

In another embodiment of the present invention, a method of preparing a dehydration catalyst is provided. The method comprises contacting:
(a) a dehydration catalyst precursor mixture comprising: one or more amorphous phosphate salt precursors, one or more crystalline phosphate salts, and one or more non-phosphate salts; wherein said one or more crystalline phosphate salts and said one or more non-phosphate salts are substantially chemically inert to said one or more amorphous phosphate salt precursors; wherein said one or more amorphous phosphate salt precursors consist essentially of: i) one or more monovalent cations; and ii) one or more phosphate anions selected from the group represented by molecular formulae (V) and (VI):

$$[H_2P_yO_{(3y+1)}]^{p-} \qquad (V)$$

$$[PO_3]_z^{z-} \qquad (VI);$$

wherein y is any integer number equal to or greater than 1 and z is any integer number equal to or greater than 3; wherein said one or more amorphous phosphate salt precursors are neutrally charged;

wherein said one or more crystalline phosphate salts consists essentially of: i) one or more polyvalent cations, and ii) one or more phosphate anions selected from the group represented by molecular formula (II):

$$[H_{(f-2g-h)}P_fO_{(4f-g)}]^{(2f+h)-} \qquad (II);$$

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and wherein said one or more non-phosphate salts consist essentially of: i) one or more polyvalent cations, and ii) one or more non-phosphate anions selected from the group represented by molecular formulae (III) and (IV):

$$[H_{(a-2b)}S_cO_{(4c-b)}]^{(2c-a)-} \qquad (III)$$

$$[Ta_{2d}O_{(5d+e)}]^{2e-} \qquad (IV);$$

wherein a and b are positive integers or zero; wherein c, d, and e are positive integers; wherein (a−2b) is equal to or greater than zero; wherein (2c−a) is greater than zero; wherein said one or more non-phosphate salts are neutrally charged; with
(b) a gas mixture comprising water;
wherein the water partial pressure in said gas mixture is equal to or greater than about 4.0 bar; wherein said contacting step between said dehydration catalyst precursor mixture and said gas mixture is performed at a temperature equal to or greater than about 250° C.; and wherein one or more amorphous phosphate salts are produced as a result of said one or more amorphous phosphate salt precursors being contacted with said water vapor.

In yet another embodiment of the present invention, a method of preparing a dehydration catalyst is provided. The method comprises contacting:
(a) a dehydration catalyst precursor mixture comprising: i) $KH_2PO_4$ or $(KPO_3)_n$, ii) $Ba_2P_2O_7$, and iii) $BaSO_4$; with
(b) a gas mixture comprising water vapor;
wherein the water partial pressure in said gas mixture is equal to or greater than the water partial pressure at the triple point of $KH_2PO_4$ or $(KPO_3)_n$; wherein said contacting step between said dehydration catalyst precursor mixture and said gas mixture is performed at a temperature equal to or greater than the temperature at the triple point of $KH_2PO_4$ or $(KPO_3)_n$; and wherein one or more amorphous phosphate salts are produced as a result of said $KH_2PO_4$ or $(KPO_3)_n$ being contacted with said water vapor.

BRIEF DESCRIPTION OF THE DRAWINGS

For a more complete understanding of the disclosure, reference should be made to the following detailed description and drawing Figures.

Figure 1:
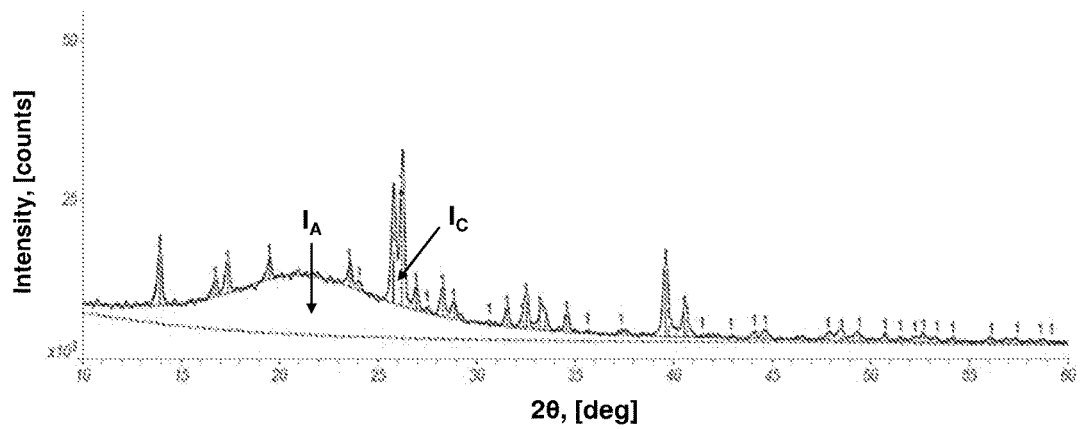
FIG. 1 illustrates the calculation of amorphous content in the dehydration catalyst using an XRD technique. The separate amorphous ($I_A$) and crystalline ($I_C$) contributions to the scattering pattern are determined using a profile-fitting technique, after appropriate background subtraction.

While the disclosed catalysts and methods are susceptible of embodiments in various forms, there are illustrated in the figures (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

I. Definitions

As used herein, the term "catalyst" refers to either a pre-reaction catalyst (also called a catalyst precursor mixture) or an in-situ catalyst. The pre-reaction catalyst is the catalyst loaded into the chemical reactor, and the in-situ catalyst is the catalyst present in the reactor during the reaction. In general, a catalyst increases the reaction rate without being consumed in the reaction. Finally, a pre-reaction catalyst can remain unchanged during the reaction or undergo in-situ physical or chemical transformations during the reaction that can change its physical and chemical properties and become an in-situ catalyst.

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "condensed phosphate" refers to any salts containing one or several P—O—P bonds generated by corner sharing of $PO_4$ tetrahedra.

As used herein, the term "polyphosphate" refers to any condensed phosphates with a linear structure; i.e. containing linear P—O—P linkages by corner sharing of $PO_4$ tetrahedra leading to the formation of finite chains.

As used herein, the term "cyclophosphate" refers to any condensed phosphate with a cyclic structure.

As used herein, the term "hydrated" refers to a hydrated crystalline salt or hydrated crystalline compound that contains a specific number of water molecules per formula unit of the salt or compound.

As used herein, the term "monovalent cation" refers to any cation with a positive charge of +1.

As used herein, the term "polyvalent cation" refers to any cation with a positive charge equal or greater than +2.

As used herein, the term "anion" refers to any atom or group of covalently-bonded atoms having a negative charge.

As used herein, the term "heteropolyanion" refers to any anion with covalently bonded $XO_p$ and $YO_r$ polyhedra, and thus comprises X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the term "amorphous" refers to the state of any condensed phase material that lacks the long-range order characteristic of a crystalline material. An amorphous material can be either an amorphous solid or a liquid. In the context of the present invention, materials with more than 50 wt % of amorphous content are considered amorphous materials.

As used herein, the term "crystalline" refers to the state of any condensed phase material whose constituents are arranged in a highly ordered microscopic structure, forming a crystal lattice with long-range order. In the context of the present invention, materials with less than 50 wt % of amorphous content are considered crystalline materials.

As used herein, the term "chemically inert" materials refers to materials which remain in the same chemical form, under equilibrium conditions, when contacted with another material or materials. In the context of the present invention, more than about 90 wt % of the material should remain in the same chemical form to be considered a "substantially chemically inert" material and more than about 98 wt % of the material should remain in the same chemical form to be considered an "essentially chemically inert" material.

As used herein, the term "antioxidant" refers to a molecule capable of terminating radical chain processes by either donating a hydrogen atom or the reaction of an olefinic bond to form a stabilized organic radical and thus terminate radical chain processes. Non limiting examples of antioxidants comprise thiols, polyphenols, butylated hydroxy toluene (BHA), and butylated hydroxy anisole (BHA).

As used herein, the terms "LA" refers to lactic acid, "AA" refers to acrylic acid, "AcH" refers to acetaldehyde, and "PA" refers to propionic acid.

As used herein, the term "conversion" in % is defined as [hydroxypropionic acid, hydroxypropionic acid derivatives, or mixtures thereof flow rate in (mol/min)–hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]×100. For the purposes of this invention, the term "conversion" means molar conversion, unless otherwise noted.

As used herein, the term "yield" in % is defined as [product flow rate out (mol/min)/hydroxypropionic acid, hydroxypropionic acid derivatives, or mixtures thereof flow rate in (mol/min)]×100. For the purposes of this invention, the term "yield" means molar yield, unless otherwise noted.

As used herein, the term "selectivity" in % is defined as [Yield/Conversion]×100. For the purposes of this invention, the term "selectivity" means molar selectivity, unless otherwise noted.

As used herein, the term "total carbon balance" is defined as: [((mol carbon monoxide out+mol carbon dioxide out+mol methane out)+(2×(mol acetic acid out+mol acetaldehyde out+mol ethane out+mol ethylene out))+(3×(mol acrylic acid out+mol propionic acid out+mol hydroxypropionic acid out+mol hydroxyacetone out)+(5×mol 2,3 pentanedione out)+(6×mol acrylic acid dimer out))/(3×mol hydroxypropionic acid in)]×100. If hydroxypropionic acid derivative is used instead of hydroxypropionic acid, the above formula needs to be adjusted according to the number of carbon atoms in the hydroxypropionic acid derivative.

As used herein, the term "Gas Hourly Space Velocity" or "GHSV" in $h^{-1}$ is defined as 60×[Total gas flow rate (mL/min)/catalyst empty bed volume (mL)]. The total gas flow rate is calculated under Standard Temperature and Pressure conditions (STP; 0° C. and 1 atm).

As used herein, the term "Weight Hourly Space Velocity" or "WHSV" in $h^{-1}$ is defined as 60×[Total LA flow rate (g/min)/catalyst weight (g)].

As used herein, the term "Liquid Hourly Space Velocity" or "LHSV" in $h^{-1}$ is defined as 60×[Total liquid flow rate (mL/min)/catalyst bed volume (mL)].

As used herein, the term "bio-based" material refers to a renewable material.

As used herein, the term "renewable material" refers to a material that is produced from a renewable resource.

As used herein, the term "renewable resource" refers to a resource that is produced via a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Natural resources, such as crude oil, coal, natural gas, and peat, which take longer than 100 years to form, are not considered renewable resources. Because at least part of the material of the invention is derived from a renewable resource, which can sequester carbon dioxide, use of the material can reduce global warming potential and fossil fuel consumption.

As used herein, the term "petroleum-based" material refers to a material that is produced from fossil material, such as petroleum, natural gas, coal, etc.

II. Catalysts for the Conversion of Hydroxypropionic Acid or its Derivatives to Acrylic Acid or its Derivatives Unexpectedly, it has been found that catalysts comprising a mixture of: 1) partially dehydrated dihydrogen monophosphates of monovalent cations in the amorphous state, 2) crystalline polyphosphates of polyvalent cations, and 3) non-phosphate salts of polyvalent cations (e.g. sulfates, tantalates) can dehydrate hydroxypropionic acid, hydroxypropionic acid derivatives, or mixtures thereof to acrylic acid, acrylic acid derivatives, or mixtures thereof with high: 1) yield and selectivity for acrylic acid, acrylic acid derivatives, or mixtures thereof, i.e., low amount and few side products; 2) efficiency, i.e., performance in short residence time; and 3) longevity. As a non limiting example, the amorphous state of said mixture of partially dehydrated dihydrogen monophosphates can be formed reversibly when crystalline phosphate salts (e.g. monophosphates, polyphosphates, or cyclophosphates) of monovalent cations with molar ratio of phosphorus to cations of about 1 are contacted with water at elevated water partial pressure and temperature. The applicants also found unexpectedly, that in order to dehydrate hydroxypropionic acid, hydroxypropionic acid derivatives, or mixtures thereof to acrylic acid, acrylic acid derivatives, or mixtures thereof, the dehydration catalyst of the present invention needs to be in the presence of sufficient water vapor, contrary to common belief in the art of performing dehydration reactions under dry conditions. Although not wishing to be bound by any theory, applicants hypothesize that the water vapor is required to avoid full dehydration of the dihydrogen monophosphate salts to condensed phosphates under operation conditions, maintaining the Brønsted acid sites that are required for the selective acid-catalyzed dehydration of hydroxypropionic acid and its derivatives to acrylic acid and its derivatives.

In one embodiment of the present invention, the dehydration catalyst comprises: (a) one or more amorphous phosphate salts consisting essentially of: i) one or more cations, and ii) one or more phosphate anions selected from the group represented by empirical formula (I):

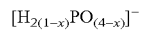   (I);

wherein x is any real number equal to or greater than 0 and equal to or less than 1; wherein said one or more amorphous phosphate salts are neutrally charged;
(b) one or more crystalline phosphate salts consisting essentially of: i) one or more cations, and ii) one or more phosphate anions selected from the group represented by molecular formula (II):

$$[H_{(f-2g-h)}P_fO_{(4f-g)}]^{(2f+h)-} \qquad (II);$$

wherein f is a positive integer; wherein g is a positive integer or zero; wherein h is an integer; wherein (f–2g–h) is equal to or greater than zero; wherein (4f–g) is greater than zero; wherein (2f+h) is greater than zero; wherein (4h/f) is equal to or greater than −2 and equal to or less than 1; wherein said one or more crystalline phosphate salts are neutrally charged; and
(c) one or more non-phosphate salts consisting essentially of: i) one or more cations, and ii) one or more non-phosphate anions selected from the group represented by molecular formulae (III) and (IV):

$$[H_{(a-2b)}S_cO_{(4c-b)}]^{(2c-a)-} \qquad (III)$$

$$[Ta_{2d}O_{(5d+e)}]^{2e-} \qquad (IV);$$

wherein a and b are positive integers or zero; wherein c, d, and e are positive integers; wherein (a–2b) is equal to or greater than zero; wherein (2c–a) is greater than zero; wherein said one or more non-phosphate salts are neutrally charged; and wherein said one or more crystalline phosphate salts and said one or more non-phosphate salts are substantially chemically inert to said one or more amorphous phosphate salts. In another embodiment of the present invention, said one or more cations of said one or more amorphous phosphate salts are selected from the group consisting of monovalent cations, polyvalent cations, and mixtures thereof. In another embodiment of the present invention, said one or more cations of said one or more amorphous phosphate salts are selected from the group consisting of monovalent cations. In another embodiment of the present invention, said one or more cations of said one or more crystalline phosphate salts are selected from the group consisting of monovalent cations, polyvalent cations, and mixtures thereof. In another embodiment of the present invention, said one or more cations of said one or more crystalline phosphate salts are selected from the group consisting of polyvalent cations. In another embodiment of the present invention, said one or more cations of said one or more non-phosphate salts are selected from the group consisting of monovalent cations, polyvalent cations, and mixtures thereof. In another embodiment of the present invention, said one or more cations of said one or more non-phosphate salts are selected from the group consisting of polyvalent cations.

In one embodiment of the present invention, the dehydration catalyst comprises: (a) one or more amorphous phosphate salts consisting essentially of: i) one or more monovalent cations, and ii) one or more phosphate anions selected from the group represented by empirical formula (I):

$$[H_{2(1-x)}PO_{(4-x)}]^- \qquad (I);$$

wherein x is any real number equal to or greater than 0 and equal to or less than 1; wherein said one or more amorphous phosphate salts are neutrally charged;
(b) one or more crystalline phosphate salts consisting essentially of: i) one or more polyvalent cations, and ii) one or more phosphate anions selected from the group represented by molecular formula (II):

$$[H_{(f-2g-h)}P_fO_{(4f-g)}]^{(2f+h)-} \qquad (II);$$

wherein f is a positive integer; wherein g is a positive integer or zero; wherein h is an integer; wherein (f–2g–h) is equal to or greater than zero; wherein (4f–g) is greater than zero; wherein (2f+h) is greater than zero; wherein (4h/f) is equal to or greater than −2 and equal to or less than 1; wherein said one or more crystalline phosphate salts are neutrally charged; and
(c) one or more non-phosphate salts consisting essentially of: i) one or more polyvalent cations, and ii) one or more non-phosphate anions selected from the group represented by molecular formulae (III) and (IV):

$$[H_{(a-2b)}S_cO_{(4c-b)}]^{(2c-a)-} \qquad (III)$$

$$[Ta_{2d}O_{(5d+e)}]^{2e-} \qquad (IV);$$

wherein a and b are positive integers or zero; wherein c, d, and e are positive integers; wherein (a–2b) is equal to or greater than zero; wherein (2c–a) is greater than zero; wherein said one or more non-phosphate salts are neutrally charged; and wherein said one or more crystalline phosphate salts and said one or more non-phosphate salts are substantially chemically inert to said one or more amorphous phosphate salts. In another embodiment of the present invention, said one or more crystalline phosphate salts and said one or more non-phosphate salts are essentially chemically inert to said one or more amorphous phosphate salts. In another embodiment of the present invention, said one or more crystalline phosphate salts and said one or more non-phosphate salts are chemically inert to said one or more amorphous phosphate salts. In yet another embodiment of the present invention, the weight fraction of said one or more amorphous phosphate salts in said dehydration catalyst is between about 0.1 and about 0.8.

The amorphous phosphate salts that comprise one or more phosphate anions represented by empirical formula (I) can be a mixture of amorphous monophosphates and polyphosphates of different length (e.g. $M^IH_2PO_4$, $M^I_2H_2P_2O_7$, $M^I_3H_2P_3O_{10}$, $M^I_4H_2P_4O_{13}$, ... $M^I_nH_2P_nO_{(3n+1)}$; wherein $M^I$ is a monovalent cation). As a non limiting example, this mixture can be produced by partial dehydration of dihydrogen monophosphates or by partial hydrolysis of condensed phosphates with molar ratio of phosphorus to cations of about 1. The amorphous phosphate salts can also comprise any hydrated form of said monophosphates and polyphosphates. In the context of the present invention, the variable x in empirical formula (I) refers either to the composition of single species within said mixture of monophosphates and polyphosphates or to the average composition of said mixture.

In the context of the present invention, a phosphate salt or a mixture of phosphate salts with more than 50 wt % of amorphous content (or less than 50 wt % of crystalline content) are considered amorphous phosphate salts. The amorphous content can be determined by any method known to those skilled in the art, such as, by way of example and not limitation, x-ray diffraction (XRD), infrared spectroscopy (IR), Raman spectroscopy, differential scanning calorimetry (DSC), or solid-state nuclear magnetic resonance (NMR) spectroscopy. As an illustration, in a method based on an XRD technique (see FIG. 1), the separate crystalline ($I_C$) and amorphous ($I_A$) contributions on the X-ray scattering pattern are determined using a profile-fitting technique. This deconvolution of the scattering pattern into the separate contributions can be performed using Gaussian, Lorentzian, Voigt, or related functions known to those skilled in the art. Then, the amorphous content, $X_A$, is determined by calculating the ratio between the area of scattered intensity for the amorphous contribution ($I_A$) and the area of the total scattered intensity (crystalline plus amorphous contributions, $I_T = I_C + I_A$) for a defined Bragg angle range (e.g. $2\theta = 5°$ to $50°$, Cu-radiation $\lambda = 1.54059$ Å, in the context of the current invention), i.e.

$$X_A = \frac{I_A}{I_C + I_A} \times 100 \text{ wt \%}.$$

In another embodiment of the present invention, at least one of said one or more amorphous phosphate salts of said dehydration catalyst is replaced by one or more crystalline phosphate salts of monovalent cations consisting essentially of: i) one or more monovalent cations, and ii) one or more phosphate anions selected from the group represented by empirical formula (I):

$$[H_{2(1-x)}PO_{(4-x)}]^- \qquad (I);$$

wherein x is any real number equal to or greater than 0 and equal to or less than 1; wherein said one or more crystalline phosphate salts of monovalent cations are neutrally charged.

In one embodiment of the present invention, said one or more amorphous phosphate salts of said dehydration catalyst are selected from the group represented by empirical formula (Ia):

$$M^I H_{2(1-x)}PO_{(4-x)} \qquad (Ia);$$

wherein $M^I$ is a monovalent cation; wherein x is any real number equal to or greater than 0 and equal to or less than 1. In another embodiment of the present invention, at least one of said one or more amorphous phosphate salts of said dehydration catalyst is replaced by one or more crystalline phosphate salts represented by empirical formula (Ia); wherein $M^I$ is a monovalent cation; wherein x is any real number equal to or greater than 0 and equal to or less than 1.

In one embodiment of the present invention, said one or more amorphous phosphate salts of said dehydration catalyst are selected from the group represented by empirical formula (Ib):

$$M^I_w N^I_{(1-w)} H_{2(1-x)} PO_{(4-x)} \qquad (Ib);$$

wherein $M^I$ and $N^I$ are two different monovalent cations; wherein x is any real number equal to or greater than 0 and equal to or less than 1; wherein w is any real number greater than 0 and less than 1. In another embodiment of the present invention, at least one of said one or more amorphous phosphate salts of said dehydration catalyst is replaced by one or more crystalline phosphate salts represented by empirical formula (Ib); wherein $M^I$ and $N^I$ are two different monovalent cations; wherein x is any real number equal to or greater than 0 and equal to or less than 1; wherein w is any real number greater than 0 and less than 1.

In another embodiment of the present invention, at least one of said one or more amorphous phosphate salts of said dehydration catalyst is a hydrated salt. In another embodiment of the present invention, at least one of said one or more crystalline phosphate salts is a hydrated salt. In another embodiment of the present invention, at least one of said one or more non-phosphate salts is a hydrated salt. A hydrated salt contains a specific number of water molecules per formula unit of the salt. Non limiting examples of hydrated salts are hemihydrated, monohydrated, sesquihydrated, dehydrated, trihydrated, tetrahydrated, pentahydrated, hexahydrated, heptahydrated, octahydrated, nonahydrated, nonahydrated, and decahydrated salts.

In the context of the present invention, "one or more cations" refers to different types of cations and "one or more anions" refers to different types of anions. Non limiting examples of cations are metallic cations, organo-metallic cations, ammonium, substituted ammonium, oxycations, and other cations known by those skilled in the art. Non limiting examples of substituted ammonium and other cations are isopropylammonium, ethylenediammonium, sarcosinium, L-histidinium, glycinium, and 4-aminopyridinium. Non limiting examples of oxycations are pervanadyl and vanadyl ions.

Non limiting examples of monovalent cations of said one or more amorphous phosphate salts are cations of alkali metals, organo-metallic cations, ammonium, substituted ammonium, oxycations, and other cations known by those skilled in the art. In one embodiment of the present invention, said one or more monovalent cations of said one or more amorphous phosphate salts are selected from the group consisting of $Li^+$, $Na^+$, $K^+$, $Rb^+$, $Cs^+$, $Ag^+$, $Tl^+$, and mixtures thereof. In another embodiment of the present invention, said one or more monovalent cations of said one or more amorphous phosphate salts are selected from the group consisting of $K^+$, $Rb^+$, $Cs^+$, and mixtures thereof. In yet another embodiment of the present invention, said one or more monovalent cations of said one or more amorphous phosphate salts is $K^+$.

In another embodiment of the present invention, at least one of said one or more amorphous phosphate salts consists of two or more different monovalent cations selected from the group consisting of $Li^+$, $Na^+$, $K^+$, $Rb^+$, $Cs^+$, $Ag^+$, and $Tl^+$. In another embodiment of the present invention, at least one of said one or more amorphous phosphate salts consists of two or more different monovalent cations selected from the group consisting of $K^+$, $Rb^+$, and $Cs^+$.

In one embodiment of the present invention, said one or more amorphous phosphate salts are selected from the group consisting of $KH_{2(1-x)}PO_{(4-x)}$, $RbH_{2(1-x)}PO_{(4-x)}$, $CsH_{2(1-x)}PO_{(4-x)}$, any of their hydrated forms, and mixtures thereof; wherein x is any real number equal to or greater than 0 and equal to or less than 1. In another embodiment of the present invention, the amorphous phosphate salt is $KH_{2(1-x)}PO_{(4-x)}$; wherein x is any real number equal to or greater than 0 and equal to or less than 1.

In one embodiment of the present invention, the amorphous phosphate salts are selected from the group consisting of $K_w Rb_{(1-w)} H_{2(1-x)} PO_{(4-x)}$, $K_w Cs_{(1-w)} H_{2(1-x)} PO_{(4-x)}$, $Rb_w Cs_{(1-w)} H_{2(1-x)} PO_{(4-x)}$, any of their hydrated forms, and mixtures thereof; wherein x is any real number equal to or greater than 0 and equal to or less than 1; and wherein w is any real number greater than 0 and less than 1.

Non limiting examples of said one or more polyvalent cations of said one or more crystalline phosphate salts and of said one or more non-phosphate salts are cations of alkaline earth metals, transition metals, post-transition or poor metals, and metalloids; organo-metallic cations, substituted ammonium cations, oxycations (e.g. vanadyl), and other cations known by those skilled in the art. In one embodiment of the present invention, said one or more polyvalent cations of said one or more crystalline phosphate salts and said one or more polyvalent cations of said one or more non-phosphate salts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more polyvalent cations of said one or more crystalline phosphate salts and said one or more polyvalent cations of said one or more non-phosphate salts are selected from the group consisting of the cations of the metals Mg, Ca, Sr, Ba, Y, Mn, Al, Er, and mixtures thereof. In another embodiment of the present invention, said one or more polyvalent cations of said one or more crystalline phosphate salts and said one or more polyvalent cations of said one or more non-phosphate salts are selected from the group consisting of divalent cations, trivalent cations, tetravalent cations, pentavalent cations, and mixtures thereof. In another embodiment of the present invention, said one or more polyvalent cations of said one or more crystalline phosphate salts and said one or more polyvalent cations of said one or more non-phosphate salts are selected from the group consisting of $Be^{2+}$, $Mg^{2+}$, $Ca^{2+}$, $Sr^{2+}$, $Ba^{2+}$, $Sc^{3+}$, $Y^{3+}$, $Ti^{3+}$, $Ti^{4+}$, $Zr^{2+}$, $Zr^{4+}$, $Hf^{4+}$, $V^{3+}$, $V^{4+}$, $Nb^{3+}$, $Cr^{2+}$, $Cr^{3+}$, $Mo^{3+}$, $Mo^{4+}$, $Mn^{2+}$, $Mn^{3+}$, $Re^{4+}$, $Al^{3+}$, $Ga^{3+}$, $In^{3+}$, $Si^{4+}$, $Ge^{4+}$, $Sn^{4+}$, $Pb^{4+}$, $Sb^{3+}$, $Sb^{5+}$, $Bi^{3+}$, $La^{3+}$, $Ce^{3+}$, $Ce^{4+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and mixtures thereof. In another embodiment of the present invention, said one or more polyvalent cations of said one or more crystalline phosphate salts and said one or more polyvalent cations of said one or more non-phosphate salts are selected from the group consisting of $Mg^{2+}$, $Ca^{2+}$, $Sr^{2+}$, $Ba^{2+}$, $y^{3+}$, $Mn^{2+}$, $Mn^{3+}$, $Al^{3+}$, $Er^{3+}$, and mixtures thereof. In yet another embodiment of the present invention, said one or more polyvalent cations of said one or more crystalline phosphate salts and said one or more polyvalent cations of said one or more non-phosphate salts are $Ba^{2+}$.

In one embodiment of the present invention, said one or more crystalline phosphate salts further consist of one or more monovalent cations. In another embodiment of the present invention, said one or more non-phosphate salts further consist of one or more monovalent cations. Non limiting examples of said one or more monovalent cations of said one or more crystalline phosphate salts and of said one or more non-phosphate salts are cations of alkali metals. In one embodiment of the present invention, said one or more monovalent cations of said one or more crystalline phosphate salts and said one or more monovalent cations of said one or more non-phosphate salts are selected from the group consisting of the cations of the metals Li, Na, K, Rb, Cs, Ag, Ti, and mixtures thereof; and said one or more polyvalent cations of said one or more crystalline phosphate salts and said one or more polyvalent cations of said one or more non-phosphate salts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more monovalent cations of said one or more crystalline phosphate salts and said one or more monovalent cations of said one or more non-phosphate salts are selected from the group consisting of the cations of the metals K, Rb, Cs, and mixtures thereof; and said one or more polyvalent cations of said one or more crystalline phosphate salts and said one or more polyvalent cations of said one or more non-phosphate salts are selected from the group consisting of the cations of the metals Mg, Ca, Sr, Ba, Y, Mn, Al, Er, and mixtures thereof.

In one embodiment of the present invention, said one or more phosphate anions of said one or more crystalline phosphate salts are selected from the group represented by molecular formulae (IIa) to (IIg), and mixtures thereof:

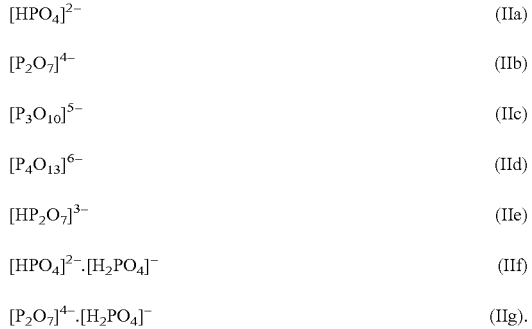

In another embodiment of the present invention, said one or more phosphate anions of said one or more crystalline phosphate salts are selected from the group represented by molecular formulae (IIa), (IIb), and mixtures thereof:

Non limiting examples of said one or more crystalline phosphate salts are phosphates of alkaline earth metals, transition metals, post-transition or poor metals, and metalloids; and phosphates of mixed alkali metals with alkaline earth metals, transition metals, post-transition or poor metals, and metalloids. In one embodiment of the present invention, said one or more crystalline phosphate salts are selected from the group consisting of $BeHPO_4$, $MgHPO_4$, $CaHPO_4$, $SrHPO_4$, $BaHPO_4$, $BeNH_4PO_4$, $Be_2P_2O_7$, $Mg_2P_2O_7$, $MgK_2P_2O_7$, $Mg_3K_2(P_2O_7)_2$, $Ca_2P_2O_7$, $CaK_2P_2O_7$, $Ca_3K_2(P_2O_7)_2$, $Ca_5K_2(P_2O_7)_3$, $CaRb_2P_2O_7$, $CaCs_2P_2O_7$, $CaMgP_2O_7$, $Ca_3(NH_4)_2(P_2O_7)_2$, $Ca_5(NH_4)_2(P_2O_7)_3$, $Sr_2P_2O_7$, $SrK_2P_2O_7$, $SrRb_2P_2O_7$, $SrCs_2P_2O_7$, $SrMgP_2O_7$, $Ba_2P_2O_7$, $BaMgP_2O_7$, $BaCaP_2O_7$, $Sc_4(P_2O_7)_3$, $ScKP_2O_7$, $ScRbP_2O_7$, $ScCsP_2O_7$, $YKP_2O_7$, $YRbP_2O_7$, $YCsP_2O_7$, $TiP_2O_7$, $Ti_2Ba(P_2O_7)_2$, $ZrP_2O_7$, $ZrMgP_2O_7$, $HfP_2O_7$, $V_4(P_2O_7)_3$, $VKP_2O_7$, $VRbP_2O_7$, $VCsP_2O_7$, $V_2Sr(P_2O_7)_2$, $V_2Ba(P_2O_7)_2$, $Nb_2Mg(P_2O_7)_2$, $Cr_4(P_2O_7)_3$, $CrHP_2O_7$, $CrNH_4P_2O_7$, $CrKP_2O_7$, $CrRbP_2O_7$, $CrCsP_2O_7$, $Cr_2Mg(P_2O_7)_2$, $CrCaP_2O_7$, $Cr_2Ca(P_2O_7)_2$, $Cr_2Sr(P_2O_7)_2$, $CrBaP_2O_7$, $Cr_2Ba(P_2O_7)_2$, $MoP_2O_7$, $MoKP_2O_7$, $MoRbP_2O_7$, $MoCsP_2O_7$, $Mo_2Ba(P_2O_7)_2$, $Mn_2P_2O_7$, $MnHP_2O_7$, $MnK_2P_2O_7$, $MnKP_2O_7$, $2Mn_2P_2O_7 \cdot Mn_2KP_3O_{10}$, $MnRb_2P_2O_7$, $MnRbP_2O_7$, $MnCsP_2O_7$, $MnCaP_2O_7$, $MnSrP_2O_7$, $MnBaP_2O_7$, $ReP_2O_7$, $AlNH_4P_2O_7$, $AlKP_2O_7$, $AlRbP_2O_7$, $GaNH_4P_2O_7$, $GaKP_2O_7$, $GaRbP_2O_7$, $InKP_2O_7$, $InRbP_2O_7$, $InCsP_2O_7$, $In_2Ca(P_2O_7)_2$, $In_2Sr(P_2O_7)_2$, $In_2Ba(P_2O_7)_2$, $SiP_2O_7$, $GeP_2O_7$, $SnP_2O_7$, $PbP_2O_7$, $Sb^{V}Sb^{III}(P_2O_7)_2$, $Bi_4(P_2O_7)_3$, $BiHP_2O_7$, $La_4(P_2O_7)_3$, $LaHP_2O_7$, $LaKP_2O_7$, $CeP_2O_7$, $Gd_4(P_2O_7)_3$, $GdKP_2O_7$, $GdRbP_2O_7$, $GdCsP_2O_7$, $TbKP_2O_7$, $TbRbP_2O_7$, $TbCsP_2O_7$, $DyKP_2O_7$, $DyRbP_2O_7$, $DyCsP_2O_7$, $HoKP_2O_7$, $HoRbP_2O_7$, $HoCsP_2O_7$, $ErKP_2O_7$, $ErRbP_2O_7$, $ErCsP_2O_7$, $TmKP_2O_7$, $TmRbP_2O_7$, $TmCsP_2O_7$, $YbHP_2O_7$, $YbKP_2O_7$, $YbRbP_2O_7$, $YbCsP_2O_7$, $LuKP_2O_7$, $LuRbP_2O_7$, $LuCsP_2O_7$, $Be_2RbP_3O_{10}$, $Ca_2KP_3O_{10}$, $Ca_2RbP_3O_{10}$, $Ca_2CsP_3O_{10}$, $Sr_2KP_3O_{10}$, $Sr_2RbP_3O_{10}$, $Sr_2CsP_3O_{10}$, $Ba_2KP_3O_{10}$, $Ba_2RbP_3O_{10}$, $Ba_2CsP_3O_{10}$, $Y_5(P_3O_{10})_3$, $VCsP_3O_{10}$, $CrCs_2P_3O_{10}$, $Cr_3K(P_3O_{10})_2$, $Cr_3Rb(P_3O_{10})_2$, $Cr_3Cs(P_3O_{10})_2$, $MnCs_2P_3O_{10}$, $AlCs_2P_3O_{10}$, $Al_3Cs(P_3O_{10})_2$, $GaCs_2P_3O_{10}$, $In_5(P_3O_{10})_3$, $La_5(P_3O_{10})_3$, $Pr_5(P_3O_{10})_3$, $Nd_5(P_3O_{10})_3$, $Sm_5(P_3O_{10})_3$, $Gd_5(P_3O_{10})_3$, $Er_5(P_3O_{10})_3$, $Yb_5(P_3O_{10})_3$, $Ca_3P_4O_{13}$, $Sr_3P_4O_{13}$, $Ba_3P_4O_{13}$, $Ba_2MgP_4O_{13}$, $Y_2P_4O_{13}$, $Cr_2P_4O_{13}$, $Mn_2P_4O_{13}$, $Gd_2P_4O_{13}$, $Pb_3P_4O_{13}$, Bi$_2$P$_4$O$_{13}$, La$_2$P$_4$O$_{13}$, any of their hydrated forms, and mixtures thereof. In another embodiment of the present invention, said one or more crystalline phosphate salts are selected from the group consisting of MgHPO$_4$, CaHPO$_4$, SrHPO$_4$, BaHPO$_4$, Mg$_2$P$_2$O$_7$, Ca$_2$P$_2$O$_7$, Sr$_2$P$_2$O$_7$, Ba$_2$P$_2$O$_7$, YKP$_2$O$_7$, Mn$_2$P$_2$O$_7$, MnKP$_2$O$_7$, AlKP$_2$O$_7$, ErKP$_2$O$_7$, Ca$_3$P$_4$O$_{13}$, Sr$_3$P$_4$O$_{13}$, Ba$_3$P$_4$O$_{13}$, any of their hydrated forms, and mixtures thereof.

In one embodiment of the present invention, said one or more non-phosphate anions are selected from the group represented by molecular formulae (IIIa) to (IIId), (IVa) to (IVg), and mixtures thereof:

$$[SO_4]^{2-} \quad \text{(IIIa)}$$

$$[S_2O_7]^{2-} \quad \text{(IIIb)}$$

$$[HSO_4]^{1-} \quad \text{(IIIc)}$$

$$[SO_4]^{2-}\cdot[HSO_4]^{-} \quad \text{(IIId)}$$

$$[Ta_2O_6]^{2-} \quad \text{(IVa)}$$

$$[Ta_2O_7]^{4-} \quad \text{(IVb)}$$

$$[Ta_2O_9]^{8-} \quad \text{(IVc)}$$

$$[Ta_2O_{10}]^{10-} \quad \text{(IVd)}$$

$$[Ta_2O_{11}]^{12-} \quad \text{(IVe)}$$

$$[Ta_4O_{11}]^{2-} \quad \text{(IVf)}$$

$$[Ta_4O_{15}]^{10-} \quad \text{(IVg)}.$$

In another embodiment of the present invention, said one or more non-phosphate anions are selected from the group represented by molecular formulae (IIIa), (IVa), and mixtures thereof:

$$[SO_4]^{2-} \quad \text{(IIIa)}$$

$$[Ta_2O_6]^{2-} \quad \text{(IVa)}.$$

Non limiting examples of said one or more non-phosphate salts are sulfates of alkaline-earth metals, tantalates of alkaline-earth metals, sulfates of mixed alkali and alkaline earth metals, and tantalates of mixed alkali and alkaline earth metals. In one embodiment of the present invention, said one or more non-phosphate salts are selected from the group consisting of CaSO$_4$, SrSO$_4$, BaSO$_4$, SrK$_2$(SO$_4$)$_2$, SrRb$_2$(SO$_4$)$_2$, Ca$_2$K$_2$(SO$_4$)$_3$, Ca$_2$Rb$_2$(SO$_4$)$_3$, Ca$_2$Cs$_2$(SO$_4$)$_3$, CaTa$_4$O$_{11}$, SrTa$_4$O$_{11}$, BaTa$_4$O$_{11}$, MgTa$_2$O$_6$, CaTa$_2$O$_6$, SrTa$_2$O$_6$, BaTa$_2$O$_6$, Mg$_2$Ta$_2$O$_7$, Ca$_2$Ta$_2$O$_7$, Sr$_2$Ta$_2$O$_7$, SrK$_2$Ta$_2$O$_7$, Ba$_2$Ta$_2$O$_7$, Ba$_3$Ta$_2$O$_8$, Mg$_4$Ta$_2$O$_9$, Ca$_4$Ta$_2$O$_9$, Sr$_4$Ta$_2$O$_9$, Ba$_4$Ta$_2$O$_9$, Ca$_5$Ta$_2$O$_{10}$, Ca$_2$KTa$_3$O$_{10}$, Ca$_2$RbTa$_3$O$_{10}$, Ca$_2$CsTa$_3$O$_{10}$, Sr$_2$KTa$_3$O$_{10}$, Sr$_2$RbTa$_3$O$_{10}$, Sr$_2$CsTa$_3$O$_{10}$, MgsTa$_4$O$_{15}$, Sr$_5$Ta$_4$O$_{15}$, BasTa$_4$O$_{15}$, Sr$_2$KTa$_5$O$_{15}$, Ba$_2$KTa$_5$O$_{15}$, Sr$_6$Ta$_2$O$_{11}$, Ba$_6$Ta$_2$O$_{11}$, any of their hydrated forms, and mixtures thereof. In another embodiment of the present invention, said one or more non-phosphate salts are selected from the group consisting of CaSO$_4$, CaTa$_2$O$_6$, SrSO$_4$, SrTa$_2$O$_6$, BaSO$_4$, BaTa$_2$O$_6$, any of their hydrated forms, and mixtures thereof. In yet another embodiment of the present invention, said one or more non-phosphate salts are selected from the group consisting of BaSO$_4$, BaTa$_2$O$_6$, any of their hydrated forms, and mixtures thereof.

In another embodiment of the present invention, said one or more amorphous phosphate salts are selected from the group consisting of KH$_{2(1-x)}$PO$_{(4-x)}$, RbH$_{2(1-x)}$PO$_{(4-x)}$, CsH$_{2(1-x)}$PO$_{(4-x)}$, K$_w$Rb$_{(1-w)}$H$_{2(1-x)}$PO$_{(4-x)}$, K$_w$Cs$_{(1-w)}$H$_{2(1-x)}$PO$_{(4-x)}$, Rb$_w$Cs$_{(1-w)}$H$_{2(1-x)}$PO$_{(4-x)}$, any of their hydrated forms, and mixtures thereof; wherein x is any real number equal to or greater than 0 and equal to or less than 1 and wherein w is any real number greater than 0 and less than 1; said one or more crystalline phosphate salts are selected from the group consisting of Ca$_2$P$_2$O$_7$, CaHPO$_4$, Sr$_2$P$_2$O$_7$, SrHPO$_4$, Ba$_2$P$_2$O$_7$, BaHPO$_4$, any of their hydrated forms, and mixtures thereof; and said one or more non-phosphate salts are selected from the group consisting of CaSO$_4$, CaTa$_2$O$_6$, SrSO$_4$, SrTa$_2$O$_6$, BaSO$_4$, BaTa$_2$O$_6$, any of their hydrated forms, and mixtures thereof. In another embodiment of the present invention, said one or more amorphous phosphate salts is KH$_{2(1-x)}$PO$_{(4-x)}$, wherein x is any real number equal to or greater than 0 and equal to or less than 1; said one or more crystalline phosphate salts is Ba$_2$P$_2$O$_7$; and said one or more non-phosphate compounds is BaSO$_4$.

In one embodiment of the present invention, said dehydration catalyst further comprises silicon oxide (SiO$_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In yet another embodiment of the present invention, said silicon oxide has a specific surface area of less than about 10 m$^2$/g. In another embodiment of the present invention, said dehydration catalyst comprises KH$_{2(1-x)}$PO$_{(4-x)}$, BaSO$_4$, Ba$_2$P$_2$O$_7$, and amorphous silica; wherein x is any real number equal to or greater than 0 and equal to or less than 1. In another embodiment of the present invention, said dehydration catalyst consists essentially of KH$_{2(1-x)}$PO$_{(4-x)}$, BaSO$_4$, Ba$_2$P$_2$O$_7$, and amorphous silica; wherein x is any real number equal to or greater than 0 and equal to or less than 1.

The variable x in formulae (I), (Ia), and (Ib) is any real number equal to or greater than 0 and equal to or less than 1. In one embodiment of the present invention, x is equal to about 0. In another embodiment of the present invention, x is equal to about 1. In another embodiment of the present invention, x is less than about 0.8. In another embodiment of the present invention, x is less than about 0.6. In another embodiment of the present invention, x is less than about 0.5. In another embodiment of the present invention, x is between about 0.1 and about 0.5. In another embodiment of the present invention, x is between about 0.25 and about 0.45. In another embodiment of the present invention, x is equal to about 0.4. In yet another embodiment, x is equal to about 0.4 and said one or more monovalent cations is Cs$^+$. The variable w in formula (Ib) is any real number greater than 0 and less than 1. In one embodiment of the present invention, w is less than about 0.2 or greater than about 0.8. In another embodiment of the present invention, w is less than about 0.1 or greater than about 0.9.

In one embodiment of the present invention, said one or more amorphous phosphate salts of said dehydration catalyst consist essentially of: (a) one or more monovalent cations, and (b) the phosphate anion represented by molecular formula (Ic):

wherein said one or more amorphous phosphate salts of said dehydration catalyst are neutrally charged. In another embodiment of the present invention, at least one of said one or more amorphous phosphate salts of said dehydration catalyst is replaced by one or more crystalline phosphate salts consisting essentially of: (a) one or more monovalent cations, and (b) the phosphate anion represented by molecular formula (Ic).

In one embodiment of the present invention, said one or more amorphous phosphate salts of said dehydration catalyst are selected from the group represented by molecular formula (Id):

$$M^I H_2 PO_4 \quad\quad\quad (Id);$$

wherein $M^I$ is a monovalent cation. In another embodiment of the present invention, at least one of said one or more amorphous phosphate salts of said dehydration catalyst is replaced by one or more crystalline phosphate salts represented by molecular formula (Id).

In one embodiment of the present invention, said one or more amorphous phosphate salts of said dehydration catalyst are selected from the group represented by molecular formula (Ie):

$$M_w^I N_{(1-w)}^I H_2 PO_4 \quad\quad\quad (Ie);$$

wherein $M^I$ and $N^I$ are two different monovalent cations; wherein w is any real number greater than 0 and less than 1. In another embodiment of the present invention, at least one of said one or more amorphous phosphate salts of said dehydration catalyst is replaced by one or more crystalline phosphate salts represented by molecular formula (Ie).

In one embodiment of the present invention, said one or more amorphous phosphate salts of said dehydration catalyst consist essentially of: (a) one or more monovalent cations, and (b) the phosphate anion represented by empirical formula (If):

$$[PO_3]^- \quad\quad\quad (If);$$

wherein said one or more amorphous phosphate salts of said dehydration catalyst are neutrally charged. In another embodiment of the present invention, at least one of said one or more amorphous phosphate salts of said dehydration catalyst is replaced by one or more crystalline phosphate salts consisting essentially of: (a) one or more monovalent cations, and (b) the phosphate anion represented by empirical formula (If). In the context of the present invention, the anion represented by empirical formula (If) can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistrty and Technology" by D. E. C. Corbridge (2013). When the empirical formula (If) refers to the anion of long chain polyphosphate salts, the empirical formula is not precise in that it does not include the minor perturbation of excess negative charge owing to the two end-group oxygens.

In one embodiment of the present invention, said one or more amorphous phosphate salts of said dehydration catalyst are selected from the group represented by empirical formula (Ig):

$$M^I PO_3 \quad\quad\quad (Ig);$$

wherein $M^I$ is a monovalent cation. In another embodiment of the present invention, at least one of said one or more amorphous phosphate salts of said dehydration catalyst is replaced by one or more crystalline phosphate salts represented by empirical formula (Ig).

In one embodiment of the present invention, said one or more amorphous phosphate salts of said dehydration catalyst are selected from the group represented by empirical formula (Ih):

$$M_w^I N_{(1-w)}^I PO_3 \quad\quad\quad (Ih);$$

wherein $M^I$ and $N^I$ are two different monovalent cations; wherein w is any real number greater than 0 and less than 1. In another embodiment of the present invention, at least one of said one or more amorphous phosphate salts of said dehydration catalyst is replaced by one or more crystalline phosphate salts represented by empirical formula (Ih). In the context of the present invention, the salts represented by empirical formula (Ig) or (Ih) can refer either to cyclophosphate salts or to long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistrty and Technology" by D. E. C. Corbridge (2013). When the salts represented by empirical formulas (Ig) or (Ih) refer to long chain polyphosphate salts, the empirical formulae are not precise in that they do not include the minor amount of either protons or excess monovalent cations needed to produce a charge neutral structure owing to the two end group oxygens.

In one embodiment of the present invention, said dehydration catalyst further comprises one or more inert supports. Non limiting examples of inert supports are silica or silicates, alumina or aluminates, aluminosilicates, titania or titanates, zirconia or zirconates, carbons (such as activated carbon, diamond, graphite, or fullerenes), sulfates, phosphates, tantalates, ceria, other metal oxides, and mixtures thereof. In the context of the reactions expressly described herein, in one embodiment of the present invention, the inert support consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In another embodiment of the present invention, said silicon oxide has a specific surface area of less than about 10 $m^2/g$. When present, the inert support represents an amount of about 20 wt % to about 90 wt %, based on the total weight of the dehydration catalyst.

Alternative catalysts comprising one or more anions selected from the group consisting of non-phosphorus-containing anions, heteropolyanions, and phosphate adducts can be utilized for dehydrating hydroxypropionic acid, hydroxypropionic acid derivatives, or mixtures thereof to acrylic acid, acrylic acid derivatives, or mixtures thereof. Non limiting examples of non-phosphorus-containing anions are arsenates, condensed arsenates, nitrates, sulfates, condensed sulfates, borates, carbonates, chromates, condensed chromates, vanadates, niobates, tantalates, selenates, condensed silicates, condensed aluminates, germanates, condensed germanates, molybdates, condensed molybdates, and other monomeric oxyanions or polyoxyanions that may be apparent to those having ordinary skill in the art. Non limiting examples of heteropolyanions are heteropolyphosphates, such as arsenatophosphates, phosphoaluminates, phosphoborates, phosphochromates, phosphomolybdates, phosphosilicates, phosphosulfates, phosphotungstates, and others that may be apparent to those having ordinary skill in the art. Non limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art.

III. Catalyst Preparation Methods

In one embodiment of the present invention, the method of preparing the dehydration catalyst comprises contacting: (a) a dehydration catalyst precursor mixture comprising: one or more amorphous phosphate salt precursors, one or more crystalline phosphate salts, and one or more non-phosphate salts; wherein said one or more crystalline phosphate salts and said one or more non-phosphate salts are substantially chemically inert to said one or more amorphous phosphate salt precursors;
wherein said one or more amorphous phosphate salt precursors consist essentially of: i) one or more cations, and ii) one or more phosphate anions selected from the group represented by molecular formulae (V) and (VI):

$$[H_2P_yO_{(3y+1)}]^{y-} \quad (V)$$

$$[PO_3]_z^{z-} \quad (VI);$$

wherein y is any integer number equal to or greater than 1 and z is any integer number equal to or greater than 3; wherein said one or more amorphous phosphate salt precursors are neutrally charged;
wherein said one or more crystalline phosphate salts consists essentially of: i) one or more cations, and ii) one or more phosphate anions selected from the group represented by molecular formula (II):

$$[H_{(f-2g-h)}P_gO_{(4f-g)}]^{(2f+h)-} \quad (II);$$

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and
wherein said one or more non-phosphate salts consist essentially of: i) one or more cations, and ii) one or more non-phosphate anions selected from the group represented by molecular formulae (III) and (IV):

$$[H_{(a-2b)}S_cO_{(4c-b)}]^{(2c-a)-} \quad (III)$$

$$[Ta_{2d}O_{(5d+e)}]^{2e-} \quad (IV);$$

wherein a and b are positive integers or zero; wherein c, d, and e are positive integers; wherein (a−2b) is equal to or greater than zero; wherein (2c−a) is greater than zero; wherein said one or more non-phosphate salts are neutrally charged; with
(b) a gas mixture comprising water vapor;
wherein the water partial pressure in said gas mixture is equal to or greater than the water partial pressure at the triple point of at least one of said one or more amorphous phosphate salt precursors; wherein said contacting step between said dehydration catalyst precursor mixture and said gas mixture is performed at a temperature equal to or greater than the temperature at the triple point of at least one of said one or more amorphous phosphate salt precursors; and wherein one or more amorphous phosphate salts are produced as a result of said one or more amorphous phosphate salt precursors being contacted with said water vapor. In another embodiment of the present invention, said one or more cations of said one or more amorphous phosphate salt precursors are selected from the group consisting of monovalent cations, polyvalent cations, and mixtures thereof. In another embodiment of the present invention, said one or more cations of said one or more amorphous phosphate salt precursors are selected from the group consisting of monovalent cations. In another embodiment of the present invention, said one or more cations of said one or more crystalline phosphate salts are selected from the group consisting of monovalent cations, polyvalent cations, and mixtures thereof. In another embodiment of the present invention, said one or more cations of said one or more crystalline phosphate salts are selected from the group consisting of polyvalent cations. In another embodiment of the present invention, said one or more cations of said one or more non-phosphate salts are selected from the group consisting of monovalent cations, polyvalent cations, and mixtures thereof. In another embodiment of the present invention, said one or more cations of said one or more non-phosphate salts are selected from the group consisting of polyvalent cations.

In one embodiment of the present invention, the method of preparing the dehydration catalyst comprises contacting: (a) a dehydration catalyst precursor mixture comprising: one or more amorphous phosphate salt precursors, one or more crystalline phosphate salts, and one or more non-phosphate salts; wherein said one or more crystalline phosphate salts and said one or more non-phosphate salts are substantially chemically inert to said one or more amorphous phosphate salt precursors; wherein said one or more amorphous phosphate salt precursors consist essentially of: i) one or more monovalent cations, and ii) one or more phosphate anions selected from the group represented by molecular formulae (V) and (VI):

$$[H_2P_yO_{(3y+1)}]^{y-} \quad (V)$$

$$[PO_3]_z^{z-} \quad (VI);$$

wherein y is any integer number equal to or greater than 1 and z is any integer number equal to or greater than 3; wherein said one or more amorphous phosphate salt precursors are neutrally charged;
wherein said one or more crystalline phosphate salts consists essentially of: i) one or more polyvalent cations, and ii) one or more phosphate anions selected from the group represented by molecular formula (II):

$$[H_{(f-2g-h)}P_gO_{(4f-g)}]^{(2f+h)-} \quad (II);$$

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and
wherein said one or more non-phosphate salts consist essentially of: i) one or more polyvalent cations, and ii) one or more non-phosphate anions selected from the group represented by molecular formulae (III) and (IV):

$$[H_{(a-2b)}S_cO_{(4c-b)}]^{(2c-a)-} \quad (III)$$

$$[Ta_{2d}O_{(5d+e)}]^{2e-} \quad (IV);$$

wherein a and b are positive integers or zero; wherein c, d, and e are positive integers; wherein (a−2b) is equal to or greater than zero; wherein (2c−a) is greater than zero; wherein said one or more non-phosphate salts are neutrally charged; with
(b) a gas mixture comprising water vapor;
wherein the water partial pressure in said gas mixture is equal to or greater than the water partial pressure at the triple point of at least one of said one or more amorphous phosphate salt precursors; wherein said contacting step between said dehydration catalyst precursor mixture and said gas mixture is performed at a temperature equal to or greater than the temperature at the triple point of at least one of said one or more amorphous phosphate salt precursors; and wherein one or more amorphous phosphate salts are produced as a result of said one or more amorphous phosphate salt precursors being contacted with said water vapor. In another embodiment of the present invention, said one or more crystalline phosphate salts and said one or more non-phosphate salts are essentially chemically inert to said one or more amorphous phosphate salt precursors. In another embodiment of the present invention, said one or more crystalline phosphate salts and said one or more non-phosphate salts are chemically inert to said one or more amorphous phosphate salt precursors. In yet another embodiment of the present invention, the weight fraction of said one or more amorphous phosphate salt precursors in said dehydration catalyst precursor mixture is between about 0.1 and about 0.8. In the context of the present invention, the anion represented by molecular formula (VI) can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistrty and Technology" by D. E. C. Corbridge (2013). When the molecular formula (VI) refers to the anion of long chain polyphosphate salts, the molecular formula is not precise in that it does not include the minor perturbation of excess negative charge owing to the two end-group oxygens.

Figure 2:
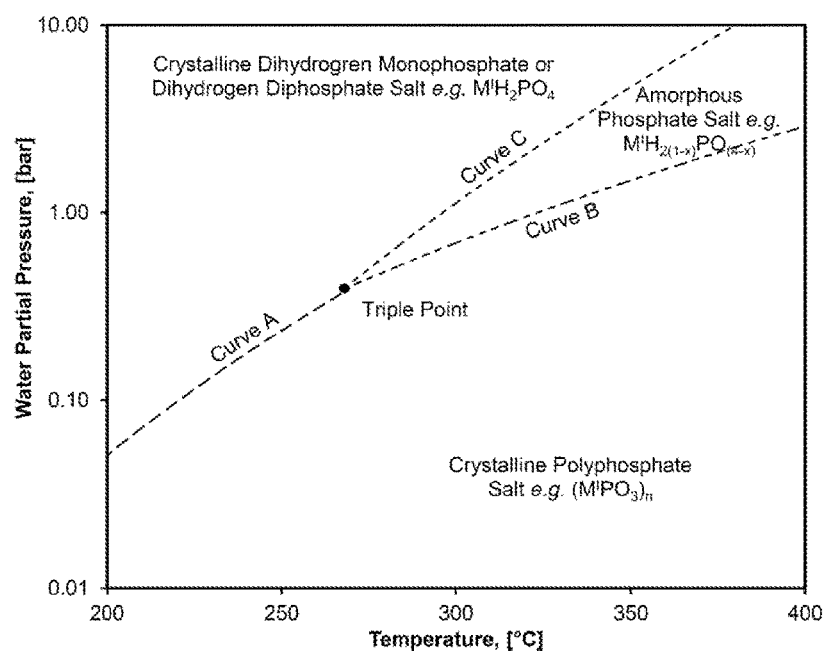
FIG. 2 illustrates a typical water partial pressure versus temperature phase equilibrium diagram of a dehydration catalyst (amorphous phosphate salt) and its precursor phosphate salts (crystalline phosphate salts). The triple point is located in the interception of the three phase boundary curves. $M^I$ is a monovalent cation. The reported values of water partial pressure are only an illustration and do not represent the real values for every specific dehydration catalyst described in the current invention.

In the context of the present invention, the triple point is the temperature and water partial pressure at which three phases: crystalline dihydrogen monophosphate or dihydrogen diphosphate salt, crystalline polyphosphate salt, and amorphous phosphate salt coexist in thermodynamic equilibrium. By way of example, and not limitation, the triple point can be located by determining the interception of two (out of three) phase boundary curves in the water partial pressure versus temperature phase equilibrium diagram (see FIG. 2):

Curve A: phase boundary between i) crystalline dihydrogen monophosphate or crystalline dihydrogen diphosphate salt and ii) crystalline polyphosphate salt, at low temperatures and water partial pressures (e.g. below about 248° C. and 0.85 bar for potassium salts, below about 267° C. and 0.35 bar for cesium salts);

Curve B: phase boundary between i) crystalline polyphosphate salt and ii) amorphous phosphate salt at high temperatures and medium water partial pressures (e.g. above about 248° C. and 0.85 bar for potassium salts, above about 267° C. and 0.35 bar for cesium salts); and Curve C: phase boundary between i) crystalline dihydrogen monophosphate or crystalline dihydrogen diphosphate salt and ii) amorphous phosphate salt at high temperatures and high water partial pressures.

The phase boundary curves can be determined by any method known to those skilled in the art, such as, by way of example and not limitation, in-situ x-ray diffraction (XRD), thermal analysis (e.g. thermogravimetric analysis, differential thermal analysis, and differential scanning calorimetry), Raman spectroscopy, infrared spectroscopy (IR), nuclear magnetic resonance (NMR) spectroscopy, or the methods described in Taninouchi, Y.-k., et al., *J. Electrochem. Soc.* 156:B572-B579 (2009); or Ikeda, A. and Haile, S. M., *Solid State Ionics* 2012, 213:63-71 (2012) (all incorporated herein by reference). As an illustration, in a method based on the in-situ XRD technique, a precursor phosphate salt is contacted at high temperature (e.g. 450° C.) with a gas stream consisting of an inert gas (e.g. nitrogen, helium, or air) and water vapor at a specific water partial pressure until equilibrium is achieved. Then, the temperature is gradually decreased while monitoring changes on x-ray diffraction patterns, until a phase transition is observed. The same procedure is repeated at different water partial pressures and the transition temperatures are recorded. The water partial pressures (in logarithmic scale) are plotted against the transition temperatures (in linear scale) and fitted to the Arrhenius equation ($\log_{10}(P_{H_2O})=A+B/T$). Finally, the triple point is calculated by determining the interception point between the two phase boundary curves (i.e. curve A and curve B in FIG. 2).

In one embodiment of the present invention, the temperature during said contacting step between said dehydration catalyst precursor mixture and said gas mixture is equal to or greater than the temperature at the triple point of at least one of said one or more precursor phosphate salts. In another embodiment of the present invention, the temperature during said contacting step between said dehydration catalyst precursor mixture and said gas mixture is equal to or greater than the lowest triple point temperature of said one or more precursor phosphate salts. In another embodiment of the present invention, the temperature during said contacting step between said dehydration catalyst precursor mixture and said gas mixture is equal to or greater than the highest triple point temperature of said one or more precursor phosphate salts. In another embodiment of the present invention, the temperature during said contacting step between said dehydration catalyst precursor mixture and said gas mixture is equal to or greater than the average temperature between the lowest triple point temperature and the highest triple point temperature of said one or more precursor phosphate salts. In another embodiment of the present invention, the temperature during said contacting step between said dehydration catalyst precursor mixture and said gas mixture is at least 10° C. greater than the temperature at the triple point of at least one of said one or more precursor phosphate salts. In another embodiment of the present invention, the temperature during said contacting step between said dehydration catalyst precursor mixture and said gas mixture is at least 50° C. greater than the temperature at the triple point of at least one of said one or more precursor phosphate salts. In another embodiment of the present invention, the temperature during said contacting step between said dehydration catalyst precursor mixture and said gas mixture is at least 100° C. greater than the temperature at the triple point of at least one of said one or more precursor phosphate salts.

In one embodiment of the present invention, the water partial pressure in said gas mixture is equal to or greater than the water partial pressure at the triple point of at least one of said one or more precursor phosphate salts. In another embodiment of the present invention, the water partial pressure in said gas mixture is equal to or greater than the lowest triple point water partial pressure of said one or more precursor phosphate salts. In another embodiment of the present invention, the water partial pressure in said gas mixture is equal to or greater than the highest triple point water partial pressure of said one or more precursor phosphate salts. In another embodiment of the present invention, the water partial pressure in said gas mixture is equal to or greater than the average water partial pressure between the lowest triple point water partial pressure and the highest triple point water partial pressure of said one or more precursor phosphate salts. In one embodiment of the present invention, the water partial pressure in said gas mixture is at least 1 bar greater than the water partial pressure at the triple point of at least one of said one or more precursor phosphate salts. In one embodiment of the present invention, the water partial pressure in said gas mixture is at least 2 bar greater than the water partial pressure at the triple point of at least one of said one or more precursor phosphate salts. In one embodiment of the present invention, the water partial pressure in said gas mixture is at least 5 bar greater than the water partial pressure at the triple point of at least one of said one or more precursor phosphate salts.

In another embodiment of the present invention, a method of preparing a dehydration catalyst comprises contacting:
(a) a dehydration catalyst precursor mixture comprising: one or more amorphous phosphate salt precursors, one or more crystalline phosphate salts, and one or more non-phosphate salts; wherein said one or more crystalline phosphate salts and said one or more non-phosphate salts are substantially chemically inert to said one or more amorphous phosphate salt precursors; wherein said one or more amorphous phosphate salt precursors consist essentially of: i) one or more monovalent cations; and ii) one or more phosphate anions selected from the group represented by molecular formulae (V) and (VI):

  (V)

  (VI);

wherein y is any integer number equal to or greater than 1 and z is any integer number equal to or greater than 3; wherein said one or more amorphous phosphate salt precursors are neutrally charged;
wherein said one or more crystalline phosphate salts consists essentially of: i) one or more polyvalent cations, and ii) one or more phosphate anions selected from the group represented by molecular formula (II):

  (II);

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and
wherein said one or more non-phosphate salts consist essentially of: i) one or more polyvalent cations, and ii) one or more non-phosphate anions selected from the group represented by molecular formulae (III) and (IV):

  (III)

  (IV);

wherein a and b are positive integers or zero; wherein c, d, and e are positive integers; wherein (a−2b) is equal to or greater than zero; wherein (2c−a) is greater than zero; wherein said one or more non-phosphate salts are neutrally charged; with
(b) a gas mixture comprising water;
wherein the water partial pressure in said gas mixture is equal to or greater than about 4.0 bar; wherein said contacting step between said dehydration catalyst precursor mixture and said gas mixture is performed at a temperature equal to or greater than about 250° C.; and wherein one or more amorphous phosphate salts are produced as a result of said one or more amorphous phosphate salt precursors being contacted with said water vapor. In another embodiment of the present invention, said one or more crystalline phosphate salts and said one or more non-phosphate salts are essentially chemically inert to said one or more amorphous phosphate salt precursors. In another embodiment of the present invention, said one or more crystalline phosphate salts and said one or more non-phosphate salts are chemically inert to said one or more amorphous phosphate salt precursors. In yet another embodiment of the present invention, the weight fraction of said one or more amorphous phosphate salt precursors in said dehydration catalyst precursor mixture is between about 0.1 and about 0.8.

In another embodiment of the present invention, a method of preparing a dehydration catalyst comprises contacting:
(a) a dehydration catalyst precursor mixture comprising: one or more amorphous phosphate salt precursors, one or more crystalline phosphate salts, and one or more non-phosphate salts; wherein said one or more crystalline phosphate salts and said one or more non-phosphate salts are substantially chemically inert to said one or more amorphous phosphate salt precursors;
wherein said one or more amorphous phosphate salt precursors consist essentially of: i) one or more monovalent cations selected from the group consisting of $K^+$, $Rb^+$, $Cs^+$, and mixtures thereof; and ii) one or more phosphate anions selected from the group represented by molecular formulae (V) and (VI):

  (V)

  (VI);

wherein y is any integer number equal to or greater than 1 and z is any integer number equal to or greater than 3; wherein said one or more amorphous phosphate salt precursors are neutrally charged;
wherein said one or more crystalline phosphate salts consists essentially of: i) one or more polyvalent cations, and ii) one or more phosphate anions selected from the group represented by molecular formula (II):

  (II);

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged; and
wherein said one or more non-phosphate salts consist essentially of: i) one or more polyvalent cations, and ii) one or more non-phosphate anions selected from the group represented by molecular formulae (III) and (IV):

  (III)

  (IV);

wherein a and b are positive integers or zero; wherein c, d, and e are positive integers; wherein (a−2b) is equal to or greater than zero; wherein (2c−a) is greater than zero; wherein said one or more non-phosphate salts are neutrally charged; with
(b) a gas mixture comprising water;
wherein the water partial pressure in said gas mixture is equal to or greater than about 0.8 bar; wherein said contacting step between said dehydration catalyst precursor mixture and said gas mixture is performed at a temperature equal to or greater than about 250° C.; and wherein one or more amorphous phosphate salts are produced as a result of said one or more amorphous phosphate salt precursors being contacted with said water vapor. In another embodiment of the present invention, said one or more crystalline phosphate salts and said one or more non-phosphate salts are essentially chemically inert to said one or more amorphous phosphate salt precursors. In another embodiment of the present invention, said one or more crystalline phosphate salts and said one or more non-phosphate salts are chemically inert to said one or more amorphous phosphate salt precursors. In yet another embodiment of the present invention, the weight fraction of said one or more amorphous phosphate salt precursors in said dehydration catalyst precursor mixture is between about 0.1 and about 0.8.

In the context of the present invention, "one or more cations" refers to different types of cations and "one or more anions" refers to different types of anions. Non limiting examples of cations are metallic cations, organo-metallic cations, ammonium, substituted ammonium, oxycations, and other cations known by those skilled in the art. Non limiting examples of substituted ammonium and other cations are isopropylammonium, ethylenediammonium, sarcosinium, L-histidinium, glycinium, and 4-aminopyridinium. Non limiting examples of oxycations are pervanadyl and vanadyl ions.

Non limiting examples of monovalent cations of said one or more amorphous phosphate salt precursors are cations of alkali metals, organo-metallic cations, ammonium, substituted ammonium, oxycations (e.g. pervanadyl), and other cations known by those skilled in the art. In one embodiment of the present invention, said one or more monovalent cations of said one or more amorphous phosphate salt precursors are selected from the group consisting of Li, $Na^+$, $K^+$, $Rb^+$, $Cs^+$, $Ag^+$, $Tl^+$, and mixtures thereof. In another embodiment of the present invention, said one or more monovalent cations of said one or more amorphous phosphate salt precursors are selected from the group consisting of $K^+$, $Rb^+$, $Cs^+$, and mixtures thereof. In yet another embodiment of the present invention, said one or more monovalent cations of said one or more amorphous phosphate salt precursors is $K^+$.

In another embodiment of the present invention, at least one of said one or more amorphous phosphate salt precursors consists of two or more different monovalent cations selected from the group consisting of Li, $Na^+$, $K^+$, $Rb^+$, $Cs^+$, $Ag^+$, and $Tl^+$. In another embodiment of the present invention, at least one of said one or more amorphous phosphate salt precursors consists of two or more different monovalent cations selected from the group consisting of $K^+$, $Rb^+$, and $Cs^+$.

In one embodiment of the present invention, said one or more phosphate anions of said one or more amorphous phosphate salt precursors are selected from the group represented by molecular formulae (Va), (Vb), (IVc), (Vd), (VIa), (VIb), (VIc) and mixtures thereof:

  (Va)

  (Vb)

  (Vc)

  (Vd)

  (VIa)

  (VIb)

  (VIc);

wherein n is any integer equal to or greater than 3. In the context of the present invention, the anion represented by molecular formula (VIc) can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistry and Technology" by D. E. C. Corbridge (2013). When the molecular formula (VIc) refers to the anion of long chain polyphosphate salts, the molecular formula is not precise in that it does not include the minor perturbation of excess negative charge owing to the two end-group oxygens.

Non limiting examples of amorphous phosphate salt precursors are dihydrogen monophosphates, dihydrogen diphosphates, dihydrogen triphosphates, dihydrogen tetraphosphates, tricyclophosphates, tetracyclophosphates, pentacyclophosphates, hexacyclophosphates, octacyclophosphates, decacyclophosphates, and linear polyphosphates of alkali metals or mixed alkali metals. In one embodiment of the present invention, said one or more amorphous phosphate salt precursors are selected from the group consisting of $LiH_2PO_4$, $Li_2H_2P_2O_7$, $Li_3P_3O_9$, $Li_4P_4O_{12}$, $Li_6P_6O_{18}$, $LiSPsO_{24}$, $(LiPO_3)_n$, $NaH_2PO_4$, $Na_2H_2P_2O_7$, $Na_3H_2P_3O_{10}$, $Na_3P_3O_9$, $Na_5P_5O_{15}$, $Na_4P_4O_{12}$, $Na_6P_6O_{18}$, $NasPsO_{24}$, $Na_{12}P_{12}O_{36}$, $(NaPO_3)_n$, $KH_2PO_4$, $K_2H_2P_2O_7$, $K_3H_2P_3O_{10}$, $K_4H_2P_4O_{13}$, $K_3P_3O_9$, $K_4P_4O_{12}$, $K_6P_6O_{18}$, $KsPsO_{24}$, $K_{10}P_{10}O_{30}$, $(KPO_3)_n$, $RbH_2PO_4$, $Rb_2H_2P_2O_7$, $Rb_3H_2P_3O_{10}$, $Rb_4H_2P_4O_{13}$, $Rb_3P_3O_9$, $Rb_4P_4O_{12}$, $Rb_6P_6O_{18}$, $RbsPsO_{24}$, $(RbPO_3)_n$, $CsH_2PO_4$, $Cs_2H_2P_2O_7$, $Cs_3H_2P_3O_{10}$, $Cs_4H_2P_4O_{13}$, $Cs_3P_{3O9}$, $Cs_4P_4O_{12}$, $Cs_6P_6O_{18}$, $CssPsO_{24}$, $(CsPO_3)$, $NaK_3(H_2P_2O_7)_2$, $LiK_2P_3O_9$, $LiNa_2P_3O_9$, $Na_2KP_3O_9$, $Na_2RbP_3O_9$, $Na_2CsP_3O_9$, $Na_3KP_4O_{12}$, $Na_2K_2P_4O_{12}$, $Na_2Rb_2P_4O_{12}$, $Na_3CsP_4O_{12}$, $Li_3Na_3P_6O_{18}$, $Li_3K_3P_6O_{18}$, $Li_2K_4P_6O_{18}$, $Li_3Na_3P_6O_{18}$, $Li_3K_3P_6O_{18}$, $Li_3Rb_3P_6O_{18}$, $Li_3Cs_3P_6O_{18}$, $Na_4Rb_2P_6O_{18}$, $Na_4Cs_2P_6O_{18}$, $LiNa_7PsO_{24}$, $Na_6K_4P_{10}O_{30}$, $(LiK(PO_3)_2)$, $(LiRb(PO_3)_2)_n$, $(Li_2Rb(PO_3)_3)_n$, $(LiCs(PO_3)_2)$, $(Li_2Cs(PO_3)_3)_n$, any of their hydrated forms, and mixtures thereof. In another embodiment of the present invention, said one or more amorphous phosphate salt precursors are selected from the group consisting of $LiH_2PO_4$, $(LiPO_3)_n$, $NaH_2PO_4$, $(NaPO_3)_n$, $KH_2PO_4$, $(KPO_3)_n$, $RbH_2PO_4$, $(RbPO_3)_n$, $CsH_2PO_4$, $(CsPO_3)_n$, any of their hydrated forms, and mixtures thereof. In yet another embodiment of the present invention, said one or more amorphous phosphate salt precursors are selected from the group consisting of $KH_2PO_4$, $(KPO_3)_n$, any of their hydrated forms, and mixtures thereof. In the context of the present invention, the amorphous phosphate salt precursors represented by the formulae $(M^IPO_3)_n$, $(M^IN^I(PO_3)_2)_n$, or $(M^I_2N^I(PO_3)_3)_n$, wherein $M^I$ and $N^I$ are two different monovalent cations, can be either cyclophosphates or long-chain linear polyphosphates.

Non limiting examples of said one or more polyvalent cations of said one or more crystalline phosphate salts and of said one or more non-phosphate salts are cations of alkaline earth metals, transition metals, post-transition or poor metals, and metalloids; organo-metallic cations, substituted ammonium cations, oxycations (e.g. vanadyl), and other cations known by those skilled in the art. In one embodiment of the present invention, said one or more polyvalent cations of said one or more crystalline phosphate salts and said one or more polyvalent cations of said one or more non-phosphate salts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more polyvalent cations of said one or more crystalline phosphate salts and said one or more polyvalent cations of said one or more non-phosphate salts are selected from the group consisting of the cations of the metals Mg, Ca, Sr, Ba, Y, Mn, Al, Er, and mixtures thereof. In another embodiment of the present invention, said one or more polyvalent cations of said one or more crystalline phosphate salts and said one or more polyvalent cations of said one or more non-phosphate salts are selected from the group consisting of divalent cations, trivalent cations, tetravalent cations, pentavalent cations, and mixtures thereof. In another embodiment of the present invention, said one or more polyvalent cations of said one or more crystalline phosphate salts and said one or more polyvalent cations of said one or more non-phosphate salts are selected from the group consisting of $Be^{2+}$, $Mg^{2+}$, $Ca^{2+}$, $Sr^{2+}$, $Ba^{2+}$, $Sc^{3+}$, $Y^{3+}$, $Ti^{3+}$, $Ti^{4+}$, $Zr^{2+}$, $Zr^{4+}$, $Hf^{4+}$, $V^{3+}$, $V^{4+}$, $Nb^{3+}$, $Cr^{2+}$, $Cr^{3+}$, $Mo^{3+}$, $Mo^{4+}$, $Mn^{2+}$, $Mn^{3+}$, $Re^{4+}$, $Al^{3+}$, $Ga^{3+}$, $In^{3+}$, $Si^{4+}$, $Ge^{4+}$, $Sn^{4+}$, $Pb^{4+}$, $Sb^{3+}$, $Sb^{5+}$, $Bi^{3+}$, $La^{3+}$, $Ce^{3+}$, $Ce^{4+}$, $Pr^{3+}$, $Nd^{3+}$, $Sm^{3+}$, $Eu^{3+}$, $Gd^{3+}$, $T^{3+}$, $Dy^{3+}$, $Ho^{3+}$, $Er^{3+}$, $Tm^{3+}$, $Yb^{3+}$, $Lu^{3+}$, and mixtures thereof. In another embodiment of the present invention, said one or more polyvalent cations of said one or more crystalline phosphate salts and said one or more polyvalent cations of said one or more non-phosphate salts are selected from the group consisting of $Mg^{2+}$, $Ca^{2+}$, $Sr^{2+}$, $Ba^{2+}$, $Y^{3+}$, $Mn^{2+}$, $Mn^{3+}$, $Al^{3+}$, $Er^{3+}$, and mixtures thereof. In yet another embodiment of the present invention, said one or more polyvalent cations of said one or more crystalline phosphate salts and said one or more polyvalent cations of said one or more non-phosphate salts are $Ba^{2+}$. In one embodiment of the present invention, said one or more crystalline phosphate salts further consist of one or more monovalent cations. In another embodiment of the present invention, said one or more non-phosphate salts further consist of one or more monovalent cations. Non limiting examples of said one or more monovalent cations of said one or more crystalline phosphate salts and of said one or more non-phosphate salts are cations of alkali metals. In one embodiment of the present invention, said one or more monovalent cations of said one or more crystalline phosphate salts and said one or more monovalent cations of said one or more non-phosphate salts are selected from the group consisting of the cations of the metals Li, Na, K, Rb, Cs, Ag, Tl, and mixtures thereof; and said one or more polyvalent cations of said one or more crystalline phosphate salts and said one or more polyvalent cations of said one or more non-phosphate salts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more monovalent cations of said one or more crystalline phosphate salts and said one or more monovalent cations of said one or more non-phosphate salts are selected from the group consisting of the cations of the metals K, Rb, Cs, and mixtures thereof; and said one or more polyvalent cations of said one or more crystalline phosphate salts and said one or more polyvalent cations of said one or more non-phosphate salts are selected from the group consisting of the cations of the metals Mg, Ca, Sr, Ba, Y, Mn, Al, Er, and mixtures thereof.

In one embodiment of the present invention, said one or more phosphate anions of said one or more crystalline phosphate salts are selected from the group represented by molecular formulae (IIa) to (IIg), and mixtures thereof:

$[HPO_4]^{2-}$ (IIa)

$[P_2O_7]^{4-}$ (IIb)

$[P_3O_{10}]^{5-}$ (IIc)

$[P_4O_{13}]^{6-}$ (IId)

$[HP_2O_7]^{3-}$ (IIe)

$[HPO_4]^{2-} \cdot [H_2PO_4]^{-}$ (IIf)

$[P_2O_7]^{4-} \cdot [H_2PO_4]^{-}$ (IIg).

In another embodiment of the present invention, said one or more phosphate anions of said one or more crystalline phosphate salts are selected from the group represented by molecular formulae (IIa), (IIb), and mixtures thereof:

$[HPO_4]^{2-}$ (IIa)

$[P_2O_7]^{4-}$ (IIb).

Non limiting examples of said one or more crystalline phosphate salts are phosphates of alkaline earth metals, transition metals, post-transition or poor metals, and metalloids; and phosphates of mixed alkali metals with alkaline earth metals, transition metals, post-transition or poor metals, and metalloids. In one embodiment of the present invention, said one or more crystalline phosphate salts are selected from the group consisting of $BeHPO_4$, $MgHPO_4$, $CaHPO_4$, $SrHPO_4$, $BaHPO_4$, $BeNH_4PO_4$, $Be_2P_2O_7$, $Mg_2P_2O_7$, $MgK_2P_2O_7$, $Mg_3K_2(P_2O_7)_2$, $Ca_2P_2O_7$, $CaK_2P_2O_7$, $Ca_3K_2(P_2O_7)_2$, $Ca_5K_2(P_2O_7)_3$, $CaRb_2P_2O_7$, $CaCs_2P_2O_7$, $CaMgP_2O_7$, $Ca_3(NH_4)_2(P_2O_7)_2$, $Ca_5(NH_4)_2(P_2O_7)_3$, $Sr_2P_2O_7$, $SrK_2P_2O_7$, $SrRb_2P_2O_7$, $SrCs_2P_2O_7$, $SrMgP_2O_7$, $Ba_2P_2O_7$, $BaMgP_2O_7$, $BaCaP_2O_7$, $Sc_4(P_2O_7)_3$, $ScKP_2O_7$, $ScRbP_2O_7$, $ScCsP_2O_7$, $YKP_2O_7$, $YRbP_2O_7$, $YCsP_2O_7$, $TiP_2O_7$, $Ti_2Ba(P_2O_7)_2$, $ZrP_2O_7$, $ZrMgP_2O_7$, $HfP_2O_7$, $V_4(P_2O_7)_3$, $VKP_2O_7$, $VRbP_2O_7$, $VCsP_2O_7$, $V_2Sr(P_2O_7)_2$, $V_2Ba(P_2O_7)_2$, $Nb_2Mg(P_2O_7)_2$, $Cr_4(P_2O_7)_3$, $CrHP_2O_7$, $CrNH_4P_2O_7$, $CrKP_2O_7$, $CrRbP_2O_7$, $CrCsP_2O_7$, $Cr_2Mg(P_2O_7)_2$, $CrCaP_2O_7$, $Cr_2Ca(P_2O_7)_2$, $Cr_2Sr(P_2O_7)_2$, $CrBaP_2O_7$, $Cr_2Ba(P_2O_7)_2$, $MoP_2O_7$, $MoKP_2O_7$, $MoRbP_2O_7$, $MoCsP_2O_7$, $Mo_2Ba(P_2O_7)_2$, $Mn_2P_2O_7$, $MnHP_2O_7$, $MnK_2P_2O_7$, $MnKP_2O_7$, $2Mn_2P_2O_7 \cdot Mn_2KP_3O_{10}$, $MnRb_2P_2O_7$, $MnRbP_2O_7$, $MnCsP_2O_7$, $MnCaP_2O_7$, $MnSrP_2O_7$, $MnBaP_2O_7$, $ReP_2O_7$, $AlNH_4P_2O_7$, $AlKP_2O_7$, $AlRbP_2O_7$, $GaNH_4P_2O_7$, $GaKP_2O_7$, $GaRbP_2O_7$, $InKP_2O_7$, $InRbP_2O_7$, $InCsP_2O_7$, $In_2Ca(P_2O_7)_2$, $In_2Sr(P_2O_7)_2$, $In_2Ba(P_2O_7)_2$, $SiP_2O_7$, $GeP_2O_7$, $SnP_2O_7$, $PbP_2O_7$, $Sb^VSb^I(P_2O_7)_2$, $Bi_4(P_2O_7)_3$, $BiHP_2O_7$, $La_4(P_2O_7)_3$, $LaHP_2O_7$, $LaKP_2O_7$, $CeP_2O_7$, $Gd_4(P_2O_7)_3$, $GdKP_2O_7$, $GdRbP_2O_7$, $GdCsP_2O_7$, $TbKP_2O_7$, $TbRbP_2O_7$, $TbCsP_2O_7$, $DyKP_2O_7$, $DyRbP_2O_7$, $DyCsP_2O_7$, $HoKP_2O_7$, $HoRbP_2O_7$, $HoCsP_2O_7$, $ErKP_2O_7$, $ErRbP_2O_7$, $ErCsP_2O_7$, $TmKP_2O_7$, $TmRbP_2O_7$, $TmCsP_2O_7$, $YbHP_2O_7$, $YbKP_2O_7$, $YbRbP_2O_7$, $YbCsP_2O_7$, $LuKP_2O_7$, $LuRbP_2O_7$, $LuCsP_2O_7$, $Be_2RbP_3O_{10}$, $Ca_2KP_3O_{10}$, $Ca_2RbP_3O_{10}$, $Ca_2CsP_3O_{10}$, $Sr_2KP_3O_{10}$, $Sr_2RbP_3O_{10}$, $Sr_2CsP_3O_{10}$, $Ba_2KP_3O_{10}$, $Ba_2RbP_3O_{10}$, $Ba_2CsP_3O_{10}$, $Y_5(P_3O_{10})_3$, $VCsP_3O_{10}$, $CrCs_2P_3O_{10}$, $Cr_3K(P_3O_{10})_2$, $Cr_3Rb(P_3O_{10})_2$, $Cr_3Cs(P_3O_{10})_2$, $MnCs_2P_3O_{10}$, $AlCs_2P_3O_{10}$, $Al_3Cs(P_3O_{10})_2$, $GaCs_2P_3O_{10}$, $In_5(P_3O_{10})_3$, $La_5(P_3O_{10})_3$, $Pr_5(P_3O_{10})_3$, $Nd_5(P_3O_{10})_3$, $Sm_5(P_3O_{10})_3$, $Gd_5(P_3O_{10})_3$, $Er_5(P_3O_{10})_3$, $Yb_5(P_3O_{10})_3$, $Ca_3P_4O_{13}$, $Sr_3P_4O_{13}$, $Ba_3P_4O_{13}$, $Ba_2MgP_4O_{13}$, $Y_2P_4O_{13}$, $Cr_2P_4O_{13}$, $Mn_2P_4O_{13}$, $Gd_2P_4O_{13}$, $Pb_3P_4O_{13}$, $Bi_2P_4O_{13}$, $La_2P_4O_{13}$, any of their hydrated forms, and mixtures thereof. In another embodiment of the present invention, said one or more crystalline phosphate salts are selected from the group consisting of $MgHPO_4$, $CaHPO_4$, $SrHPO_4$, $BaHPO_4$, $Mg_2P_2O_7$, $Ca_2P_2O_7$, $Sr_2P_2O_7$, $Ba_2P_2O_7$, $YKP_2O_7$, $Mn_2P_2O_7$, $MnKP_2O_7$, $AlKP_2O_7$, $ErKP_2O_7$, $Ca_3P_4O_{13}$, $Sr_3P_4O_{13}$, $Ba_3P_4O_{13}$, any of their hydrated forms, and mixtures thereof.

In one embodiment of the present invention, said one or more non-phosphate anions are selected from the group represented by molecular formulae (IIIa) to (IIId), (IVa) to (IVg), and mixtures thereof:

$$[SO_4]^{2-} \quad \text{(IIIa)}$$

$$[S_2O_7]^{2-} \quad \text{(IIIb)}$$

$$[HSO_4]^{1-} \quad \text{(IIIc)}$$

$$[SO_4]^{2-}\cdot[HSO_4]^{-} \quad \text{(IIId)}$$

$$[Ta_2O_6]^{2-} \quad \text{(IVa)}$$

$$[Ta_2O_7]^{4-} \quad \text{(IVb)}$$

$$[Ta_2O_9]^{8-} \quad \text{(IVc)}$$

$$[Ta_2O_{10}]^{10-} \quad \text{(IVd)}$$

$$[Ta_2O_{11}]^{12-} \quad \text{(IVe)}$$

$$[Ta_4O_{11}]^{2-} \quad \text{(IVf)}$$

$$[Ta_4O_{15}]^{10-} \quad \text{(IVg)}.$$

In another embodiment of the present invention, said one or more non-phosphate anions are selected from the group represented by molecular formulae (IIIa), (IVa), and mixtures thereof:

$$[SO_4]^{2-} \quad \text{(IIIa)}$$

$$[Ta_2O_6]^{2-} \quad \text{(IVa)}.$$

Non limiting examples of said one or more non-phosphate salts are sulfates of alkaline-earth metals, tantalates of alkaline-earth metals, sulfates of mixed alkali and alkaline earth metals, and tantalates of mixed alkali and alkaline earth metals. In one embodiment of the present invention, said one or more non-phosphate salts are selected from the group consisting of $CaSO_4$, $SrSO_4$, $BaSO_4$, $SrK_2(SO_4)_2$, $SrRb_2(SO_4)_2$, $Ca_2K_2(SO_4)_3$, $Ca_2Rb_2(SO_4)_3$, $Ca_2Cs_2(SO_4)_3$, $CaTa_4O_{11}$, $SrTa_4O_{11}$, $BaTa_4O_{11}$, $MgTa_2O_6$, $CaTa_2O_6$, $SrTa_2O_6$, $BaTa_2O_6$, $Mg_2Ta_2O_7$, $Ca_2Ta_2O_7$, $Sr_2Ta_2O_7$, $SrK_2Ta_2O_7$, $Ba_2Ta_2O_7$, $Ba_3Ta_2O_8$, $Mg_4Ta_2O_9$, $Ca_4Ta_2O_9$, $Sr_4Ta_2O_9$, $Ba_4Ta_2O_9$, $CasTa_2O_{10}$, $Ca_2KTa_3O_{10}$, $Ca_2RbTa_3O_{10}$, $Ca_2CsTa_3O_{10}$, $Sr_2KTa_3O_{10}$, $Sr_2RbTa_3O_{10}$, $Sr_2CsTa_3O_{10}$, $MgsTa_4O_{15}$, $Sr_5Ta_4O_{15}$, $BasTa_4O_{15}$, $Sr_2KTa_5O_{11}$, $Ba_2KTa_5O_{15}$, $Sr_6Ta_2O_{11}$, $Ba_6Ta_2O_{11}$, any of their hydrated forms, and mixtures thereof. In another embodiment of the present invention, said one or more non-phosphate salts are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof. In yet another embodiment of the present invention, said one or more non-phosphate salts are selected from the group consisting of $BaSO_4$, $BaTa_2O_6$, any of their hydrated forms, and mixtures thereof.

In another embodiment of the present invention, said one or more amorphous phosphate salt precursors are selected from the group consisting of $KH_2PO_4$, $(KPO_3)_n$, $RbH_2PO_4$, $(RbPO_3)_n$, $CsH_2PO_4$, $(CsPO_3)_n$, any of their hydrated forms, and mixtures thereof; said one or more crystalline phosphate salts are selected from the group consisting of $Ca_2P_2O_7$, $CaHPO_4$, $Sr_2P_2O_7$, $SrHPO_4$, $Ba_2P_2O_7$, $BaHPO_4$, any of their hydrated forms, and mixtures thereof; and said one or more non-phosphate salts are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof. In another embodiment of the present invention, said one or more amorphous phosphate salt precursors is $KH_2PO_4$ or $(KPO_3)_n$; said one or more crystalline phosphate salts is $Ba_2P_2O_7$; and said one or more non-phosphate compounds is $BaSO_4$.

In one embodiment of the present invention, said dehydration catalyst precursor mixture further comprises silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In yet another embodiment of the present invention, said silicon oxide has a specific surface area of less than about 10 $m^2/g$. In another embodiment of the present invention, said dehydration catalyst comprises $(KPO_3)_n$, $BaSO_4$, $Ba_2P_2O_7$, and amorphous silica. In another embodiment of the present invention, said dehydration catalyst consists essentially of $(KPO_3)_n$, $BaSO_4$, $Ba_2P_2O_7$, and amorphous silica.

In one embodiment of the present invention, the method of preparing the dehydration catalyst further comprises mixing one or more inert supports with said dehydration catalyst precursor mixture before said contacting step with said gas mixture. Non limiting examples of inert supports are silica or silicates, alumina or aluminates, aluminosilicates, titania or titanates, zirconia or zirconates, carbons (such as activated carbon, diamond, graphite, or fullerenes), phosphates, sulfates, tantalates, ceria, other metal oxides, and mixtures thereof. In the context of the reactions expressly described herein, in one embodiment of the present invention, said one or more inert supports comprise silicon oxide ($SiO_2$). In another embodiment of the present invention, said one or more inert supports consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In another embodiment of the present invention, said silicon oxide has a specific surface area of less than about 10 $m^2/g$.

The method of preparing the dehydration catalyst comprises contacting said dehydration catalyst precursor mixture with a gas mixture comprising water vapor. In one embodiment of the present invention, the water partial pressure in said gas mixture is equal to or greater than about 0.4 bar. In another embodiment of the present invention, the water partial pressure in said gas mixture is equal to or greater than about 0.8 bar. In another embodiment of the present invention, the water partial pressure in said gas mixture is equal to or greater than about 4 bar. In another embodiment of the present invention, the water partial pressure in said gas mixture is between about 5 bar and about 35 bar. In another embodiment of the present invention, said contacting step is performed under a total pressure equal to or greater than about 1 bar. In another embodiment of the present invention, said contacting step is performed under a total pressure equal to or greater than about 4 bar. In yet another embodiment of the present invention, said contacting step is performed under a total pressure between about 4 bar and about 35 bar.

In another embodiment of the present invention, said contacting step between said dehydration catalyst precursor mixture and said gas mixture is performed at a temperature equal to or greater than about 250° C. In another embodiment of the present invention, said contacting step between said dehydration catalyst precursor mixture and said gas mixture is performed at a temperature between about 300° C. and about 450° C.

The method of preparing the dehydration catalyst can comprise mixing of two or more different materials. This mixing step can be performed by any method known to those skilled in the art, such as, by way of example and not limitation: solid mixing, impregnation, or co-precipitation. In the solid mixing method, the various components are physically mixed together with optional grinding using any method known to those skilled in the art, such as, by way of example and not limitation, shear, extensional, kneading, extrusion, ball milling, and others, and alternatively followed by any additional treatment or activation step. In the impregnation method, a suspension of insoluble material (e.g. inert support) is treated with a solution of catalyst soluble ingredients, and the resulting material is then treated or activated under conditions that will convert the mixture to a more active or preferred state. In the co-precipitation method, a homogenous solution of the catalyst ingredients is precipitated by the addition of additional ingredients, followed by optional filtration and heating to remove solvents and volatile materials (e.g., water, nitric acid, carbon dioxide, ammonia, or acetic acid).

Mixing of catalyst components with surfactants followed by heating can increase catalyst surface area. In one embodiment of the present invention, the method of preparing the dehydration catalyst further comprises mixing one or more surfactants with said one or more amorphous phosphate salt precursors, said one or more crystalline phosphate salts, said one or more non-phosphate salts, or said dehydration catalyst precursor mixture before said contacting step with said gas mixture. In another embodiment of the present invention, said one or more surfactants are cationic or zwitterionic. Non limiting examples of surfactants are myristyltrimethylammonium bromide, hexadecyltrimethylammonium bromide, dodecyltrimethylammonium bromide, decyltrimethylammonium bromide, and octadecyltrimethyl ammonium bromide.

Heating can promote chemical reactions, thermal decompositions, phase transitions, and/or removal of volatile materials. In one embodiment of the present invention, the method of preparing the dehydration catalyst further comprises heating said one or more amorphous phosphate salt precursors, said one or more crystalline phosphate salts, said one or more non-phosphate salts, or said dehydration catalyst precursor mixture at a temperature equal to or greater than 180° C. before said contacting step with said gas mixture. In another embodiment of the present invention, the method of preparing the dehydration catalyst further comprises heating said one or more amorphous phosphate salt precursors, said one or more crystalline phosphate salts, said one or more non-phosphate salts, or said dehydration catalyst precursor mixture at a temperature equal to or greater than 300° C. before said contacting step with said gas mixture. In another embodiment of the present invention, the method of preparing the dehydration catalyst further comprises heating said one or more amorphous phosphate salt precursors, said one or more crystalline phosphate salts, said one or more non-phosphate salts, or said dehydration catalyst precursor mixture at a temperature between about 350° C. and about 650° C. before said contacting step with said gas mixture. In another embodiment of the present invention, the method of preparing the dehydration catalyst further comprises heating said one or more amorphous phosphate salt precursors, said one or more crystalline phosphate salts, said one or more non-phosphate salts, or said dehydration catalyst precursor mixture at a temperature between about 400° C. and about 450° C. before said contacting step with said gas mixture. Said heating step is typically done using any method known to those skilled in the art, such as, by way of example and not limitation, convection, conduction, radiation, microwave heating, and others.

The heating step is performed with equipment such as, by way of example and not limitation, furnaces, atomizers, or reactors of various designs, comprising shaft furnaces, rotary kilns, hearth furnaces, fluidized bed reactors, spay dryers. The duration of said heating step is, in one embodiment of the present invention, about one hour to about seventy-two hours. In another embodiment, the duration of said heating step is between about two hours and about twelve hours. In yet another embodiment, the duration of said heating step is about four hours. In one embodiment, the temperature ramp in said heating step is between about 0.5° C./min and about 20° C./min. In another embodiment, the temperature ramp in said heating step is about 10° C./min.

In one embodiment of the present invention, the method of preparing the dehydration catalyst further comprises molding the particles of said one or more amorphous phosphate salt precursors, said one or more crystalline phosphate salts, said one or more non-phosphate salts, or said dehydration catalyst precursor mixture before said contacting step with said gas mixture. Non limiting examples of molding operations are granulation, agglomeration, compaction, pelleting, and extrusion. In another embodiment of the present invention, the method of preparing the dehydration catalyst further comprises size reduction or grinding of the particles of said one or more amorphous phosphate salt precursors, said one or more crystalline phosphate salts, said one or more non-phosphate salts, or said dehydration catalyst precursor mixture before said contacting step with said gas mixture. In one embodiment of the present invention, the method of preparing the dehydration catalyst further comprises sieving the particles of said one or more amorphous phosphate salt precursors, said one or more crystalline phosphate salts, said one or more non-phosphate salts, or said dehydration catalyst precursor mixture to select a material of specific size distribution before said contacting step with said gas mixture. In another embodiment of the present invention, the method of preparing the dehydration catalyst further comprises sieving the particles of said one or more amorphous phosphate salt precursors, said one or more crystalline phosphate salts, said one or more non-phosphate salts, or said dehydration catalyst precursor mixture to a median particle size of about 50 µm to about 500 µm. In yet another embodiment of the present invention, the method of preparing the dehydration catalyst further comprises sieving the particles of said one or more amorphous phosphate salt precursors, said one or more crystalline phosphate salts, said one or more non-phosphate salts, or said dehydration catalyst precursor mixture to a median particle size of about 100 µm to about 200 µm.

In another embodiment, the dehydration catalyst is prepared by the following steps, which comprise: (a) mixing $KH_2PO_4$, $BaSO_4$, $Ba_2P_2O_7$, and amorphous silica to produce a dehydration catalyst precursor mixture, (b) heating said dehydration catalyst precursor mixture between about 200° C. and about 650° C. for about one hour to about twelve hours, to produce a calcined dehydration catalyst precursor mixture, (c) optionally grinding and sieving said calcined dehydration catalyst precursor mixture, to produce a ground dehydration catalyst precursor mixture, and (d) contacting said calcined dehydration catalyst precursor mixture or said ground dehydration catalyst precursor mixture with a gas mixture comprising nitrogen and water vapor; wherein the water partial pressure in said gas mixture is between about 5 bar and about 15 bar and wherein said contacting step is performed at a temperature between about 325° C. and about 425° C., to produce said dehydration catalyst.

Following preparation, the catalyst can be utilized to catalyze several chemical reactions. Non limiting examples of reactions are: dehydration of lactic acid to acrylic acid (as described in further detail below); dehydration of 3-hydroxypropionic acid or 3-hydroxypropionic acid derivatives, or mixtures thereof to acrylic acid; dehydration of glycerin to acrolein; isomerization of lactic acid to 3-hydroxypropionic acid in the presence of water; reduction of hydroxypropionic acid to propionic acid or 1-propanol in the presence of hydrogen gas; dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

IV. Methods of Producing Acrylic Acid, Acrylic Acid Derivatives, or Mixtures Thereof The inventors have unexpectedly found that the method of dehydrating hydroxypropionic acid, hydroxypropionic acid derivatives, or mixtures thereof can produce high yield to and selectivity of acrylic acid, acrylic acid derivatives, or mixtures thereof when the dehydration catalyst is prepared according to the present invention and the dehydration reaction is operated under a water partial pressure of more than about 0.4 bar. Not wishing to be bound by theory, the inventors believe that the elevated water partial pressure enhances the catalyst activity due to the formation (or preservation) of Brønsted acid sites from less protonated catalyst precursors. Thus, the inventors have also unexpectedly found that the process of dehydrating hydroxypropionic acid can be more efficient in the presence of elevated water partial pressure than under low water partial pressure or atmospheric conditions usually preferred in the art.

A method for dehydrating hydroxypropionic acid, hydroxypropionic acid derivatives, or mixtures thereof to acrylic acid, acrylic acid derivatives, or mixtures thereof is provided. In one embodiment of the present invention, said hydroxypropionic acid is selected from the group consisting of lactic acid (2-hydroxypropionic), 3-hydroxypropionic acid, and mixtures thereof; and said hydroxypropionic acid derivatives are selected from the group consisting of lactic acid derivatives, 3-hydroxypropionic acid derivatives, and mixtures thereof. In another embodiment of the present invention, said hydroxypropionic acid is lactic acid and said hydroxypropionic acid derivatives are lactic acid derivatives.

Lactic acid can be D-lactic acid, L-lactic acid, or mixture thereof. Lactic acid derivatives can be metal or ammonium salts of lactic acid, alkyl esters of lactic acid, lactic acid oligomers, cyclic di-esters of lactic acid, lactic acid anhydride, 2-alkoxypropionic acids or their alkyl esters, 2-aryloxypropionic acids or their alkyl esters, 2-acyloxypropionic acids or their alkyl esters, or a mixture thereof. Non limiting examples of metal salts of lactic acid are sodium lactate, potassium lactate, and calcium lactate. Non limiting examples of alkyl esters of lactic acid are methyl lactate, ethyl lactate, butyl lactate, 2-ethylhexyl lactate, and mixtures thereof. A non limiting example of cyclic di-esters of lactic acid is dilactide. Non limiting examples of 2-alkoxypropionic acids are 2-methoxypropionic acid and 2-ethoxypropionic acid. A non limiting example of 2-aryloxypropionic acid is 2-phenoxypropionic acid. A non limiting example of 2-acyloxypropionic acid is 2-acetoxypropionic acid. In one embodiment of the present invention, the lactic acid derivative is methyl lactate. Methyl lactate can be neat or in a solution with water, methanol, or mixtures thereof.

3-hydroxypropionic acid derivatives can be metal or ammonium salts of 3-hydroxypropionic acid, alkyl esters of 3-hydroxypropionic acid, 3-hydroxypropionic acid oligomers, 3-alkoxypropionic acids or their alkyl esters, 3-aryloxypropionic acids or their alkyl esters, 3-acyloxypropionic acids or their alkyl esters, or a mixture thereof. Non limiting examples of metal salts of 3-hydroxypropionic acid are sodium 3-hydroxypropionate, potassium 3-hydroxypropionate, and calcium 3-hydroxypropionate. Non limiting examples of alkyl esters of hydroxypropionic acid are methyl 3-hydroxypropionate, ethyl 3-hydroxypropionate, butyl 3-hydroxypropionate, 2-ethylhexyl 3-hydroxypropionate, and mixtures thereof. Non limiting examples of 3-alkoxypropionic acids are 3-methoxypropionic acid and 3-ethoxypropionic acid. A non limiting example of 3-aryloxypropionic acid is 3-phenoxypropionic acid. A non limiting example of 3-acyloxypropionic acid is 3-acetoxypropionic acid.

Acrylic acid derivatives can be metal or ammonium salts of acrylic acid, alkyl esters of acrylic acid, acrylic acid oligomers, or mixtures thereof. Non limiting examples of metal salts of acrylic acid are sodium acrylate, potassium acrylate, and calcium acrylate. Non limiting examples of alkyl esters of acrylic acid are methyl acrylate, ethyl acrylate, butyl acrylate, 2-ethylhexyl acrylate, or mixtures thereof.

In one embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of $K^+$, $Rb^+$, $Cs^+$, and mixtures thereof; wherein the water partial pressure during said contacting step is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; c) an essentially chemically inert gas or essentially chemically inert liquid; and d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; c) an essentially chemically inert gas or essentially chemically inert liquid; and d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; c) an essentially chemically inert gas or essentially chemically inert liquid; and d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of $K^+$, $Rb^+$, $Cs^+$, and mixtures thereof; wherein the water partial pressure during said contacting step is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, said hydroxypropionic acid, hydroxypropionic acid derivatives, or mixtures thereof are in the gas phase, at least partially, during said contacting step with said dehydration catalyst or said dehydration catalyst precursor mixture. In another embodiment of the present invention, said hydroxypropionic acid, hydroxypropionic acid derivatives, or mixtures thereof are in the liquid phase, at least partially, during said contacting step with said dehydration catalyst or said dehydration catalyst precursor mixture.

In one embodiment of the present invention, a method of making acrylic acid is provided. The method comprises contacting: (a) a gas mixture comprising: i) hydroxypropionic acid, hydroxypropionic acid derivatives, or mixtures thereof; and ii) water vapor; with (b) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid is provided.

The method comprises contacting: (a) a gas mixture comprising: i) hydroxypropionic acid, hydroxypropionic acid derivatives, or mixtures thereof; and ii) water vapor; with (b) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a gas mixture comprising: i) hydroxypropionic acid, hydroxypropionic acid derivatives, or mixtures thereof; and ii) water vapor; with (b) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of $K^+$, $Rb^+$, $Cs^+$, and mixtures thereof; wherein the water partial pressure during said contacting step in said gas mixture is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a liquid mixture comprising hydroxypropionic acid, hydroxypropionic acid derivatives, or mixtures thereof; and (b) a gas mixture comprising water vapor; with (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a liquid mixture comprising hydroxypropionic acid, hydroxypropionic acid derivatives, or mixtures thereof; and (b) a gas mixture comprising water vapor; with (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a liquid mixture comprising hydroxypropionic acid, hydroxypropionic acid derivatives, or mixtures thereof; and (b) a gas mixture comprising water vapor; with (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of $K^+$, $Rb^+$, $Cs^+$, and mixtures thereof; wherein the water partial pressure during said contacting step in said gas mixture is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, said gas mixture further comprises an essentially chemically inert gas. In the context of the present invention, an essentially chemically inert gas is any gas that is essentially chemically inert to said hydroxypropionic acid, hydroxypropionic acid derivatives, or mixtures thereof, but not necessarily to said dehydration catalyst or said dehydration catalyst precursor mixture. Non limiting examples of essentially chemically inert gases are nitrogen, helium, argon, carbon dioxide, carbon monoxide, air, water vapor, and mixtures thereof. In another embodiment of the present invention, said essentially chemically inert gas comprises nitrogen. In yet another embodiment of the present invention, said essentially chemically inert gas consists essentially of nitrogen.

In another embodiment, said liquid mixture comprising hydroxypropionic acid, hydroxypropionic acid derivatives, or mixtures thereof can further comprise one or more essentially chemically inert liquids. Non limiting examples of essentially chemically inert liquids are water, hydrocarbons, chlorinated hydrocarbons, fluorinated hydrocarbons, brominated hydrocarbons, esters, ethers, ketones, aldehydes, acids, alcohols, or mixtures thereof. Non limiting examples of hydrocarbons are C5 to C8 linear and branched alkanes. A non limiting example of esters is ethyl acetate. A non limiting example of ethers is diphenyl ether. A non limiting example of ketones is acetone. Non limiting examples of alcohols are methanol, ethanol, and C3 to C8 linear and branched alcohols. In one embodiment of the present invention, said one or more essentially chemically inert liquids comprise water. In one embodiment of the present invention, said one or more essentially chemically inert liquids consists essentially of water.

In one embodiment of the present invention, a liquid mixture comprising hydroxypropionic acid, hydroxypropionic acid derivatives, or mixtures thereof is fed into an evaporator upstream of the catalytic reactor for the liquid mixture to become a gas mixture, at least partially, before contacting said dehydration catalyst or said dehydration catalyst precursor mixture. In another embodiment of the present invention, a liquid mixture comprising hydroxypropionic acid, hydroxypropionic acid derivatives, or mixtures thereof is fed directly into the catalytic reactor and contacted with said dehydration catalyst or said dehydration catalyst precursor mixture. In another embodiment of the present invention, an essentially chemically inert gas or an essentially chemically inert liquid is fed into the evaporator or into the catalytic reactor. The liquid mixture comprising hydroxypropionic acid, hydroxypropionic acid derivatives, or mixtures thereof and the essentially chemically inert gas or the essentially chemically inert liquid can be jointly or separately fed into said evaporator or said catalytic reactor. Non limiting examples of essentially chemically inert gases are nitrogen, helium, air, argon, carbon dioxide, carbon monoxide, water vapor, and mixtures thereof. Non limiting examples of essentially chemically inert liquids are water, hydrocarbons, chlorinated hydrocarbons, fluorinated hydrocarbons, brominated hydrocarbons, esters, ethers, ketones, aldehydes, acids, alcohols, or mixtures thereof.

In one embodiment of the present invention, a method of making acrylic acid, acrylic acid derivatives, or mixtures thereof comprises: a) providing a liquid mixture comprising hydroxypropionic acid, hydroxypropionic acid derivatives, or mixtures thereof; b) optionally combining said liquid mixture with an essentially chemically inert gas to form a liquid/gas blend; and c) contacting said liquid mixture or said liquid/gas blend with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In one embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof; b) optionally combining said liquid mixture with an essentially chemically inert gas to form a liquid/gas blend; and c) contacting said liquid mixture or said liquid/gas blend with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In one embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof; b) optionally combining said liquid mixture with an essentially chemically inert gas to form a liquid/gas blend; c) evaporating said liquid mixture or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In one embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof, wherein the hydroxypropionic acid is essentially in monomeric form in the aqueous solution; b) optionally combining said liquid mixture with an essentially chemically inert gas to form a liquid/gas blend; c) evaporating said liquid mixture or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In another embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof, wherein the hydroxypropionic acid is essentially in monomeric form in the aqueous solution, and wherein the hydroxypropionic acid, hydroxypropionic acid derivatives, or mixtures thereof comprise between about 10 wt % and about 25 wt % of the aqueous solution; b) optionally combining said liquid mixture with an essentially chemically inert gas to form a liquid/gas blend; c) evaporating said liquid mixture or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In another embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof, wherein the hydroxypropionic acid comprises oligomers in the aqueous solution; b) heating said liquid mixture at a temperature between about 50° C. and about 100° C. to hydrolyze the oligomers of the hydroxypropionic acid and produce a liquid mixture comprising monomeric hydroxypropionic acid; c) optionally combining said liquid mixture comprising monomeric hydroxypropionic acid with an essentially chemically inert gas to form a liquid/gas blend; d) evaporating said liquid mixture comprising monomeric hydroxypropionic acid or said liquid/gas blend to produce a gas mixture; and e) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In another embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof; b) optionally combining the liquid mixture with an essentially chemically inert gas to form a liquid/gas blend; c) evaporating said liquid mixture or said liquid/gas blend to produce a gas mixture; d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising acrylic acid, acrylic acid derivatives, or mixtures thereof; and e) cooling said acrylic acid mixture to produce a liquid acrylic acid composition comprising acrylic acid, acrylic acid derivatives, or mixtures thereof.

In one embodiment of the present invention, the concentration of the hydroxypropionic acid, hydroxypropionic acid derivatives, or mixtures thereof in said liquid mixture is between about 2 wt % and about 95 wt %. In another embodiment of the present invention, the concentration of the hydroxypropionic acid, hydroxypropionic acid derivatives, or mixtures thereof in said liquid mixture is between about 5 wt % and about 60 wt %. In another embodiment of the present invention, the concentration of the hydroxypropionic acid, hydroxypropionic acid derivatives, or mixtures thereof in said liquid mixture is between about 10 wt % and about 40 wt %. In yet another embodiment of the present invention, the concentration of the hydroxypropionic acid, hydroxypropionic acid derivatives, or mixtures thereof in said liquid mixture is about 20 wt %.

In one embodiment of the present invention, the liquid mixture comprises an aqueous solution of hydroxypropionic acid, hydroxypropionic acid derivatives, or mixtures thereof. In another embodiment of the present invention, the liquid mixture comprises an aqueous solution of lactic acid, lactic acid derivatives, or mixtures thereof. In another embodiment of the present invention, said lactic acid derivatives in said aqueous solution are selected from the group consisting of metal or ammonium salts of lactic acid, alkyl esters of lactic acid, lactic acid oligomers, cyclic di-esters of lactic acid, lactic acid anhydride, 2-alkoxypropionic acids or their alkyl esters, 2-aryloxypropionic acids or their alkyl esters, 2-acyloxypropionic acids or their alkyl esters, or a mixture thereof.

In one embodiment of the present invention, the concentration of the lactic acid, lactic acid derivatives, or mixtures thereof in said aqueous solution is between about 2 wt % and about 95 wt %. In another embodiment of the present invention, the concentration of the lactic acid, lactic acid derivatives, or mixtures thereof in said aqueous solution is between about 5 wt % and about 60 wt %. In another embodiment of the present invention, the concentration of the lactic acid, lactic acid derivatives, or mixtures thereof in said aqueous solution is between about 10 wt % and about 40 wt %. In another embodiment of the present invention, the concentration of the lactic acid, lactic acid derivatives, or mixtures thereof in said aqueous solution is about 20 wt %.

In another embodiment of the present invention, the liquid mixture comprises an aqueous solution of lactic acid along with lactic acid derivatives. In another embodiment of the present invention, the liquid mixture comprises less than about 30 wt % of lactic acid derivatives, based on the total weight of the liquid mixture. In another embodiment of the present invention, the liquid mixture comprises less than about 10 wt % of lactic acid derivatives, based on the total weight of the liquid mixture. In yet another embodiment of the present invention, the liquid mixture comprises less than about 5 wt % of lactic acid derivatives, based on the total weight of the liquid mixture.

Lactic acid can be in monomeric form or as oligomers in said aqueous solution of lactic acid, lactic acid derivatives, or mixtures thereof. In one embodiment of the present invention, the oligomers of the lactic acid in said aqueous solution of lactic acid, lactic acid derivatives, or mixtures thereof are less than about 30 wt % based on the total amount of lactic acid, lactic acid derivatives, or mixtures thereof. In another embodiment of the present invention, the oligomers of the lactic acid in said aqueous solution of lactic acid, lactic acid derivatives, or mixtures thereof are less than about 10 wt % based on the total amount of lactic acid, lactic acid derivatives, or mixtures thereof. In another embodiment of the present invention, the oligomers of the lactic acid in said aqueous solution of lactic acid, lactic acid derivatives, or mixtures thereof are less than about 5 wt % based on the total amount of lactic acid, lactic acid derivatives, or mixtures thereof. In yet another embodiment of the present invention, the lactic acid is essentially in monomeric form in said aqueous solution of lactic acid, lactic acid derivatives, or mixtures thereof.

The process to remove the oligomers from the aqueous solution of lactic acid, lactic acid derivatives, and mixtures thereof can comprise a purification step or hydrolysis by heating step. In one embodiment of the present invention, the heating step can involve heating the aqueous solution of lactic acid, lactic acid derivatives, or mixtures thereof at a temperature between about 50° C. and about 100° C. to hydrolyze the oligomers of the lactic acid. In another embodiment of the present invention, the heating step can involve heating the aqueous solution of lactic acid, lactic acid derivatives, or mixtures thereof at a temperature between about 95° C. and about 100° C. to hydrolyze the oligomers of the lactic acid. In another embodiment of the present invention, the heating step can involve heating the aqueous solution of lactic acid, lactic acid derivatives, or mixtures thereof at a temperature between about 50° C. and about 100° C. to hydrolyze the oligomers of the lactic acid and produce a monomeric lactic acid aqueous solution comprising at least 80 wt % of lactic acid in monomeric form based on the total amount of lactic acid, lactic acid derivatives, or mixtures thereof. In another embodiment of the present invention, the heating step can involve heating the aqueous solution of lactic acid, lactic acid derivatives, or mixtures thereof at a temperature between about 50° C. and about 100° C. to hydrolyze the oligomers of the lactic acid and produce a monomeric lactic acid aqueous solution comprising at least 95 wt % of lactic acid in monomeric form based on the total amount of lactic acid, lactic acid derivatives, or mixtures thereof. In another embodiment of the present invention, an about 88 wt % aqueous solution of lactic acid, lactic acid derivatives, or mixtures thereof is diluted with water and the oligomers are hydrolyzed to produce an aqueous solution of about 20 wt % lactic acid. The lactic acid oligomers can result in loss of acrylic acid selectivity due to their high boiling point. As the water content decreases in the aqueous solution, the loss of feed material to the catalyst reaction, due to losses in the evaporating step, increases. Additionally, lactic acid oligomers can cause coking, catalyst deactivation, and reactor plugging.

In another embodiment of the present invention, the liquid mixture comprising hydroxypropionic acid, hydroxypropionic acid derivatives, or mixtures thereof can further comprise one or more antioxidants. In another embodiment of the present invention, the liquid mixture comprising hydroxypropionic acid, hydroxypropionic acid derivatives, or mixtures thereof further comprises butylated hydroxy toluene (BHT), butylated hydroxy anisole (BHA), or mixtures thereof. In yet another embodiment of the present invention, the liquid mixture comprising hydroxypropionic acid, hydroxypropionic acid derivatives, or mixtures thereof further comprises ethylene glycol, ethanedithiol, methanol, methanethiol, or mixtures thereof.

The liquid mixture can be introduced into the evaporator or into the catalytic reactor with a simple tube or through atomization nozzles. Non limiting examples of atomization nozzles comprise fan nozzles, pressure swirl atomizers, air blast atomizers, two-fluid atomizers, rotary atomizers, and supercritical carbon dioxide atomizers. In one embodiment of the present invention, the droplets of the aqueous solution are less than about 500 am in diameter. In another embodiment of the present invention, the droplets of the aqueous solution are less than about 200 am in diameter. In yet another embodiment of the present invention, the droplets of the aqueous solution are less than about 100 μm in diameter.

In the evaporating step, said liquid mixture or said liquid/gas blend are heated to produce a gas mixture. In one embodiment of the present invention, the temperature during the evaporating step is between about 165° C. and about 450° C. In another embodiment of the present invention, the temperature during the evaporating step is between about 200° C. and about 400° C. In another embodiment of the present invention, the temperature during the evaporating step is between about 250° C. and about 375° C. In one embodiment of the present invention, the residence time in the evaporator during said evaporating step is between about 0.5 s and about 10 s. In another embodiment of the present invention, the residence time in the evaporator during said evaporating step is between about 1 s and about 5 s.

The evaporating step can be performed under vacuum, at atmospheric pressure, or at higher than atmospheric pressure. In one embodiment of the present invention, the evaporating step is performed under a total pressure of at least about 1 bar. In another embodiment of the present invention, the evaporating step is performed under a total pressure between about 5 bar and about 40 bar. In yet another embodiment of the present invention, the evaporating step is performed under a pressure between about 10 bar and about 35 bar. In yet another embodiment of the present invention, the evaporating step is performed under a total pressure of about 25 bar.

The evaporating step can be performed in various types of evaporators, such as, but not limited to, atomizer, plate heat exchanger, empty flow reactor, and fixed bed flow reactor. The evaporating step can be performed in an evaporator with the liquid mixture flowing down, or flowing up, or flowing horizontally. In one embodiment of the present invention, the evaporating step is performed in an evaporator with the liquid flowing down. Also, the evaporating step can be done in a batch form.

In one embodiment of the present invention, the material of the evaporator interior surface is selected from the group consisting of amorphous silica, quartz, other silicon oxides, borosilicate glass, silicon, and mixtures thereof. In yet another embodiment of the present invention, the material of the evaporator interior surface is amorphous silica or borosilicate glass.

In one embodiment of the present invention, the evaporating and contacting steps are combined in a single step. In another embodiment of the present invention, the evaporating and contacting steps are performed sequentially in a single reactor. In yet another embodiment of the present invention, the evaporating and contacting steps are performed sequentially in a tandem reactor.

The gas mixture comprising hydroxypropionic acid, hydroxypropionic acid derivatives, or mixtures thereof or the liquid mixture comprising hydroxypropionic acid, hydroxypropionic acid derivatives, or mixtures thereof are converted to acrylic acid, acrylic acid derivatives, and mixture thereof by contacting said mixtures with a dehydration catalyst. The dehydration catalyst can be selected from the group comprising phosphates, sulfates, tantalates, metal oxides, aluminates, silicates, aluminosilicates (e.g., zeolites), arsenates, nitrates, vanadates, niobates, selenates, arsenatophosphates, phosphoaluminates, phosphoborates, phosphochromates, phosphomolybdates, phosphosilicates, phosphosulfates, phosphotungstates, and mixtures thereof, and others that may be apparent to those having ordinary skill in the art. The dehydration catalyst can contain one or more inert supports. Non limiting examples of inert supports are silica or silicates, alumina or aluminates, aluminosilicates, titania or titanates, zirconia or zirconates, carbons (such as activated carbon, diamond, graphite, or fullerenes), sulfates, phosphates, tantalates, ceria, other metal oxides, and mixtures thereof. In one embodiment of the present invention, the dehydration catalyst is any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method").

In the context of the present invention, "contacting" refers to the action of bringing said hydroxypropionic acid, hydroxypropionic acid derivatives, or mixtures thereof in close proximity to the surface of said dehydration catalyst or dehydration catalyst precursor mixture. The hydroxypropionic acid, hydroxypropionic acid derivatives, or mixtures thereof must contact the surface of the dehydration catalyst or the dehydration catalyst precursor mixture at a rate that is slow enough for the dehydration reaction to occur, yet fast enough to avoid the degradation of hydroxypropionic acid, acrylic acid, or their derivatives to undesirable products at the temperature of said contacting step. Several parameters can be used to describe the rate of said contacting step, such as, by way of example and not limitation, WHSV, GHSV, LHSV, and weight velocity per unit of accessible catalyst surface area (WVSA) that can be calculated as the ratio of WHSV and the dehydration catalyst specific surface area (SA), (WVSA=WHSV/SA); with units: $g/m^2 \cdot h$, where g refer to g of hydroxypropionic acid, hydroxypropionic acid derivatives, or mixtures thereof. A number of methods, based on the adsorption of an inert gas, can be used to determine the accessible surface area, including, but not limited to, the static volumentric and gravimetric methods and the dynamic method that are well-known by those skilled in the art.

In one embodiment of the present invention, the hydroxypropionic acid, hydroxypropionic acid derivatives, or mixtures thereof contact the dehydration catalyst or the dehydration catalyst precursor mixture at a WVSA between about $10^4$ $g \cdot m^{-2} \cdot h^{-1}$ and about $10^{-4}$ $g \cdot m^{-2} \cdot h^{-1}$. In another embodiment of the present invention, the hydroxypropionic acid, hydroxypropionic acid derivatives, or mixtures thereof contact the dehydration catalyst or the dehydration catalyst precursor mixture at a WVSA between about $10^2$ $g \cdot m^{-2} \cdot h^{-1}$ and about $10^{-2}$ $g \cdot m^{-2} \cdot h^{-1}$. In another embodiment of the present invention, the hydroxypropionic acid, hydroxypropionic acid derivatives, or mixtures thereof contact the dehydration catalyst or the dehydration catalyst precursor mixture at a WVSA between about 10 $g \cdot m^{-2} \cdot h^{-1}$ and about 0.1 $g \cdot m^{-2} \cdot h^{-1}$ In one embodiment of the present invention, the hydroxypropionic acid, hydroxypropionic acid derivatives, or mixtures thereof contact the dehydration catalyst or the dehydration catalyst precursor mixture at a WHSV between about 0.02 $h^{-1}$ and about 10 $h^{-1}$. In another embodiment of the present invention, the hydroxypropionic acid, hydroxypropionic acid derivatives, or mixtures thereof contact the dehydration catalyst or the dehydration catalyst precursor mixture at a WHSV between about 0.2 $h^{-1}$ and about 1 $h^{-1}$. In another embodiment of the present invention, the hydroxypropionic acid, hydroxypropionic acid derivatives, or mixtures thereof contact the dehydration catalyst or the dehydration catalyst precursor mixture at a WHSV between about 0.4 $h^{-1}$ and about 0.7 $h^{-1}$. In another embodiment of the present invention, the hydroxypropionic acid, hydroxypropionic acid derivatives, or mixtures thereof contact the dehydration catalyst or the dehydration catalyst precursor mixture at a WHSV of about 0.5 $h^{-1}$.

When hydroxypropionic acid, hydroxypropionic acid derivatives, or mixtures thereof are in the gas phase during said contacting step with said dehydration catalyst or said dehydration catalyst precursor mixture, and in another embodiment of the present invention, the gas mixture comprising hydroxypropionic acid, hydroxypropionic acid derivatives, or mixtures thereof contacts the dehydration catalyst or the dehydration catalyst precursor mixture at a GHSV between about 720 $h^{-1}$ and about 36,000 $h^{-1}$. In another embodiment of the present invention, the gas mixture comprising hydroxypropionic acid, hydroxypropionic acid derivatives, or mixtures thereof contacts the dehydration catalyst or the dehydration catalyst precursor mixture at a GHSV between about 1,800 $h^{-1}$ and about 9,000 $h^{-1}$. In another embodiment of the present invention, the gas mixture comprising hydroxypropionic acid, hydroxypropionic acid derivatives, or mixtures thereof contacts the dehydration catalyst or the dehydration catalyst precursor mixture at a GHSV between about 3,600 $h^{-1}$ and about 6,000 $h^{-1}$. In another embodiment of the present invention, a gas mixture comprising hydroxypropionic acid, hydroxypropionic acid derivatives, or mixtures thereof contacts the dehydration catalyst or the dehydration catalyst precursor mixture at a GHSV of about 4,500 $h^{-1}$.

When hydroxypropionic acid, hydroxypropionic acid derivatives, or mixtures thereof are in the gas phase during said contacting step with said dehydration catalyst or said dehydration catalyst precursor mixture, and in one embodiment of the present invention, the concentration of hydroxypropionic acid, hydroxypropionic acid derivatives, or mixtures thereof before the dehydration reaction and based on the total moles in the gas mixture (calculated under STP conditions) is between about 0.5 mol % and about 50 mol %. In another embodiment of the present invention, the concentration of hydroxypropionic acid, hydroxypropionic acid derivatives, or mixtures thereof before the dehydration reaction and based on the total moles in the gas mixture (calculated under STP conditions) is between about 1 mol % and about 10 mol %. In another embodiment of the present invention, the concentration of hydroxypropionic acid, hydroxypropionic acid derivatives, or mixtures thereof before the dehydration reaction and based on the total moles in the gas mixture (calculated under STP conditions) is between about 1.5 mol % and about 3.5 mol %. In yet another embodiment of the present invention, the concentration of hydroxypropionic acid, hydroxypropionic acid derivatives, or mixtures thereof before the dehydration reaction and based on the total moles in the gas mixture (calculated under STP conditions) is about 2.5 mol %.

In one embodiment of the present invention, the temperature during said contacting step with the dehydration catalyst or the dehydration catalyst precursor mixture is greater than about 150° C. In another embodiment of the present invention, the temperature during said contacting step with the dehydration catalyst or the dehydration catalyst precursor mixture is greater than about 250° C. In another embodiment of the present invention, the temperature during said contacting step with the dehydration catalyst or the dehydration catalyst precursor mixture is between about 300° C. and about 500° C. In another embodiment of the present invention, the temperature during said contacting step with the dehydration catalyst or the dehydration catalyst precursor mixture is between about 325° C. and about 400° C. In yet another embodiment of the present invention, the temperature during said contacting step with the dehydration catalyst or the dehydration catalyst precursor mixture is between about 350° C. and about 375° C.

In one embodiment of the present invention, the temperature during said contacting step with the dehydration catalyst or the dehydration catalyst precursor mixture is equal to or greater than the temperature at the triple point of at least one of said one or more amorphous phosphate salts or said one or more precursor phosphate salts. In another embodiment of the present invention, the temperature during said contacting step with the dehydration catalyst precursor mixture is equal to or greater than the lowest triple point temperature of said one or more amorphous phosphate salts or said one or more precursor phosphate salts. In another embodiment of the present invention, the temperature during said contacting step with the dehydration catalyst or the dehydration catalyst precursor mixture is equal to or greater than the highest triple point temperature of said one or more amorphous phosphate salts or said one or more precursor phosphate salts. In another embodiment of the present invention, the temperature during said contacting step with the dehydration catalyst or the dehydration catalyst precursor mixture is equal to or greater than the average temperature between the lowest triple point temperature and the highest triple point temperature of said one or more amorphous phosphate salts or said one or more precursor phosphate salts. In another embodiment of the present invention, the temperature during said contacting step with the dehydration catalyst or the dehydration catalyst precursor mixture is at least 10° C. greater than the temperature at the triple point of at least one of said one or more amorphous phosphate salts or said one or more precursor phosphate salts. In another embodiment of the present invention, the temperature during said contacting step with the dehydration catalyst or the dehydration catalyst precursor mixture is at least 50° C. greater than the temperature at the triple point of at least one of said one or more amorphous phosphate salts or said one or more precursor phosphate salts. In another embodiment of the present invention, the temperature during said contacting step with the dehydration catalyst or the dehydration catalyst precursor mixture is at least 100° C. greater than the temperature at the triple point of at least one of said one or more amorphous phosphate salts or said one or more precursor phosphate salts.

In another embodiment of the present invention, said water partial pressure during said contacting step with the dehydration catalyst or the dehydration catalyst precursor mixture is equal to or greater than about 0.4 bar. In another embodiment of the present invention, said water partial pressure during said contacting step with the dehydration catalyst or the dehydration catalyst precursor mixture is equal to or greater than about 0.8 bar. In another embodiment of the present invention, said water partial pressure during said contacting step with the dehydration catalyst or the dehydration catalyst precursor mixture is equal to or greater than about 4 bar. In another embodiment of the present invention, said water partial pressure during said contacting step with the dehydration catalyst or the dehydration catalyst precursor mixture is between about 5 bar and about 35 bar.

In one embodiment of the present invention, the water partial pressure during said contacting step with the dehydration catalyst or the dehydration catalyst precursor mixture is equal to or greater than the water partial pressure at the triple point of at least one of said one or more amorphous phosphate salts or said one or more precursor phosphate salts. In another embodiment of the present invention, the water partial pressure during said contacting step with the dehydration catalyst or the dehydration catalyst precursor mixture is equal to or greater than the lowest triple point water partial pressure of said one or more amorphous phosphate salts or said one or more precursor phosphate salts. In another embodiment of the present invention, the water partial pressure during said contacting step with the dehydration catalyst or the dehydration catalyst precursor mixture is equal to or greater than the highest triple point water partial pressure of said one or more amorphous phosphate salts or said one or more precursor phosphate salts. In another embodiment of the present invention, the water partial pressure during said contacting step with the dehydration catalyst or the dehydration catalyst precursor mixture is equal to or greater than the average water partial pressure between the lowest triple point water partial pressure and the highest triple point water partial pressure of said one or more amorphous phosphate salts or said one or more precursor phosphate salts. In one embodiment of the present invention, the water partial pressure during said contacting step with the dehydration catalyst or the dehydration catalyst precursor mixture is at least 1 bar greater than the water partial pressure at the triple point of at least one of said one or more amorphous phosphate salts or said one or more precursor phosphate salts. In one embodiment of the present invention, the water partial pressure during said contacting step with the dehydration catalyst or the dehydration catalyst precursor mixture is at least 2 bar greater than the water partial pressure at the triple point of at least one of said one or more amorphous phosphate salts or said one or more precursor phosphate salts. In one embodiment of the present invention, the water partial pressure during said contacting step with the dehydration catalyst or the dehydration catalyst precursor mixture is at least 5 bar greater than the water partial pressure at the triple point of at least one of said one or more amorphous phosphate salts or said one or more precursor phosphate salts.

The contacting step with the dehydration catalyst or the dehydration catalyst precursor mixture can be performed under vacuum, at atmospheric pressure, or at higher than atmospheric pressure. In one embodiment of the present invention, the contacting step with the dehydration catalyst or the dehydration catalyst precursor mixture is performed under a total pressure of at least about 1 bar. In another embodiment of the present invention, the contacting step with the dehydration catalyst or the dehydration catalyst precursor mixture is performed under a total pressure between about 5 bar and about 40 bar. In another embodiment of the present invention, the contacting step with the dehydration catalyst or the dehydration catalyst precursor mixture is performed under a total pressure between about 10 bar and about 35 bar. In yet another embodiment of the present invention, the contacting step with the dehydration catalyst or the dehydration catalyst precursor mixture is performed under a total pressure of about 25 bar.

When hydroxypropionic acid, hydroxypropionic acid derivatives, or mixtures thereof are in the gas phase, and in another embodiment of the present invention, the contacting step with the dehydration catalyst or the dehydration catalyst precursor mixture is performed in a catalytic reactor with the gas mixture flowing down, flowing up, or flowing horizontally. In another embodiment of the present invention, the contacting step with the dehydration catalyst or the dehydration catalyst precursor mixture is performed in a catalytic reactor with the gas mixture flowing down. Also, the contacting step with the dehydration catalyst or the dehydration catalyst precursor mixture can be done in a batch form. In another embodiment of the present invention, the dehydration catalyst or the dehydration catalyst precursor mixture is suspended in an essentially chemically inert liquid. The contacting step with the dehydration catalyst or the dehydration catalyst precursor mixture can be performed by using different catalytic reactors known to those skilled in the art, such as, by way of example and not limitation, static reactor, stirred reactor, recirculation reactor, packed-bed flow reactor, and combinations thereof.

In one embodiment of the present invention, the contacting step with the dehydration catalyst or the dehydration catalyst precursor mixture is carried out in an apparatus, which is pressurized to ensure that all major components are in the liquid phase. In another embodiment of the present invention, the contacting step with the dehydration catalyst or the dehydration catalyst precursor mixture is carried out in an apparatus, which is operated at low temperature to ensure that all major components are in the liquid phase. In yet another embodiment of the present invention, the liquid mixture comprises an essentially chemically inert liquid. When all major components are in the liquid phase, the contacting step with the dehydration catalyst or the dehydration catalyst precursor mixture can be performed by using different catalytic reactors, known to those skilled in the art, such as, by way of example and not limitation, static reactor, fixed bed reactor, single-stage stirred tank reactor, multi-stage stirred tank reactor, multi-stage distillation column, and combinations thereof. The contacting step can be conducted batch-wise or continuously. The contacting step with the dehydration catalyst or the dehydration catalyst precursor mixture can be performed in a catalytic reactor with the liquid mixture comprising hydroxypropionic acid, hydroxypropionic acid derivatives, or mixtures thereof flowing down, flowing up, or flowing horizontally. In another embodiment of the present invention, the contacting step with the dehydration catalyst or the dehydration catalyst precursor mixture is performed in a catalytic reactor with the liquid mixture comprising hydroxypropionic acid, hydroxypropionic acid derivatives, or mixtures thereof flowing up.

In one embodiment of the present invention, the dehydration or isomerizations reactions of hydroxypropionic acid, hydroxypropionic acid derivatives or mixtures thereof occur in the aqueous phase, at least partially, and the pH of the reaction is between about 3 and about 8. In another embodiment of the present invention, the pH of the reaction in the aqueous phase is between about 4 and about 7. In yet another embodiment of the present invention, the pH of the reaction in the aqueous phase is between about 5 and about 6.

In one embodiment of the present invention, hydroxypropionic acid, hydroxypropionic acid derivatives, or mixtures thereof and water vapor contact the dehydration catalyst or the dehydration catalyst precursor mixture in a catalytic reactor with an interior surface material selected from the group consisting of amorphous silica, quartz, other silicon oxides, borosilicate glass, silicon, and mixtures thereof. In another embodiment of the present invention, hydroxypropionic acid, hydroxypropionic acid derivatives, or mixtures thereof and water vapor contact the dehydration catalyst or the dehydration catalyst precursor mixture in a catalytic reactor with an interior surface material selected from the group consisting of amorphous silica, quartz, borosilicate glass, and mixtures thereof. In another embodiment of the present invention, hydroxypropionic acid, hydroxypropionic acid derivatives, or mixtures thereof and water vapor contact the dehydration catalyst or the dehydration catalyst precursor mixture in a catalytic reactor with an interior surface material consisting essentially of borosilicate glass.

The acrylic acid mixture comprising acrylic acid, acrylic acid derivatives, or mixtures thereof produced in said contacting step with the dehydration catalyst or the dehydration catalyst precursor mixture is cooled to give a liquid acrylic acid composition as the product stream. The time required to cool the acrylic acid mixture must be controlled to reduce acrylic acid polymerization or decomposition to ethylene. In one embodiment of the present invention, the residence time of the acrylic acid mixture in the cooling step is less than about 30 s. In one embodiment of the present invention, the residence time of the acrylic acid mixture in the cooling step is between about 0.1 s and about 10 s.

The liquid acrylic acid composition comprising acrylic acid, acrylic acid derivatives, or mixtures thereof produced according with the present invention can be purified using some or all of the processes of extraction, drying, distilling, cooling, partial melting, and decanting described in US20130274518A1 (incorporated herein by reference) to produce crude and glacial acrylic acid. After purification, the crude and glacial acrylic acid can be polymerized to produce a superabsorbent polymer using processes that are similar to those described in US20130274697A1 (incorporated herein by reference).

In one embodiment of the present invention, said crude acrylic acid is esterified with an alcohol to produce an acrylate monomer. Non-limiting examples of alcohols are methanol, ethanol, butanol (n-butyl alcohol), 2-ethyl hexanol, isobutanol, tert-butyl alcohol, hexyl alcohol, octyl alcohol, isooctyl alcohol, lauryl alcohol, propyl alcohol, isopropyl alcohol, hydroxyethyl alcohol, hydroxypropyl alcohol, and polyols, such as hydroxyalkyl and alkylalkanolamine. In another embodiment of the present invention, said crude acrylic acid is esterified with methanol, ethanol, n-butyl alcohol, or 2-ethyl hexanol to produce methyl acrylate monomer, ethyl acrylate monomer, n-butyl acrylate monomer, or 2-ethylhexyl acrylate monomer, respectively. In yet another embodiment of the present invention, said methyl acrylate monomer, ethyl acrylate monomer, n-butyl acrylate monomer, or 2-ethylhexyl acrylate monomer is polymerized to produce methyl acrylate polymer, ethyl acrylate polymer, n-butyl acrylate polymer, or 2-ethylhexyl acrylate polymer, respectively. In even yet another embodiment of the present invention, said methyl acrylate monomer, ethyl acrylate monomer, n-butyl acrylate monomer, or 2-ethylhexyl acrylate monomer is co-polymerized with other monomer to produce methyl acrylate co-polymer, ethyl acrylate co-polymer, n-butyl acrylate co-polymer, or 2-ethylhexyl acrylate co-polymer, respectively. Non-limiting examples of other monomers are vinyl acetate and ethylene. In one embodiment of the present invention, said methyl acrylate polymer, ethyl acrylate polymer, n-butyl acrylate polymer, or 2-ethylhexyl acrylate polymer is blended with methyl methacrylate (MMA) to produce blends of MMA and methyl acrylate polymer, blends of MMA and ethyl acrylate polymer, blends of MMA and n-butyl acrylate polymer, or blends of MMA and 2-ethylhexyl acrylate polymer, respectively. Non-limiting applications of polymers, co-polymers, or blends are in surface coatings, paints, resins, adhesives, plastics, and dispersions. In another embodiment of the present invention, said alcohol is bio-based alcohol. In yet another embodiment of the present invention, said other monomer is bio-based monomer. In even yet another embodiment of the present invention, said MMA is bio-based MMA.

In one embodiment of the present invention, the method of making acrylic acid, acrylic acid derivatives, or mixtures thereof comprises contacting said hydroxypropionic acid, hydroxypropionic acid derivatives, and mixture thereof and said water vapor with said dehydration catalyst or said dehydration catalyst precursor mixture under conditions sufficient to produce acrylic acid, acrylic acid derivatives, or mixtures thereof in a yield of at least 50%. In another embodiment of the present invention, the method comprises contacting said hydroxypropionic acid, hydroxypropionic acid derivatives, and mixture thereof and said water vapor with said dehydration catalyst or said dehydration catalyst precursor mixture under conditions are sufficient to produce acrylic acid, acrylic acid derivatives, or mixtures thereof in a yield of at least about 70%. In another embodiment of the present invention, the method comprises contacting said hydroxypropionic acid, hydroxypropionic acid derivatives, and mixture thereof and said water vapor with said dehydration catalyst or said dehydration catalyst precursor mixture under conditions are sufficient to produce acrylic acid, acrylic acid derivatives, or mixtures thereof in a yield of at least about 80%. In another embodiment of the present invention, the method conditions are sufficient to produce acrylic acid, acrylic acid derivatives, or mixtures thereof with a selectivity of at least about 50%. In another embodiment of the present invention, the method conditions are sufficient to produce acrylic acid, acrylic acid derivatives, or mixtures thereof with a selectivity of at least about 70%. In another embodiment of the present invention, the method conditions are sufficient to produce acrylic acid, acrylic acid derivatives, or mixtures thereof with a selectivity of at least about 80%. In another embodiment of the present invention, the method conditions are sufficient to produce acrylic acid, acrylic acid derivatives, or mixtures thereof with propionic acid as an impurity, wherein the propionic acid selectivity is less than about 5%. In another embodiment of the present invention, the method conditions are sufficient to produce acrylic acid, acrylic acid derivatives, or mixtures thereof with propionic acid as an impurity, wherein the propionic acid selectivity is less than about 1%. In another embodiment of the present invention, the method conditions are sufficient to produce acrylic acid, acrylic acid derivatives, or mixtures thereof with a conversion of said hydroxypropionic acid, hydroxypropionic acid derivatives, or mixtures thereof of more than about 50%. In another embodiment of the present invention, the method conditions are sufficient to produce acrylic acid, acrylic acid derivatives, or mixtures thereof with a conversion of said hydroxypropionic acid, hydroxypropionic acid derivatives, or mixtures thereof of more than about 80%.

Among the benefits attainable by the foregoing embodiments is the low yield of side products. In one embodiment of the present invention, the conditions are sufficient to produce propionic acid in a yield of less than about 5% from hydroxypropionic acid. In another embodiment of the present invention, the conditions are sufficient to produce propionic acid in a yield of less than about 1%, from hydroxypropionic acid. In one embodiment of the present invention, the conditions are sufficient to produce each of acetic acid, pyruvic acid, 1,2-propanediol, hydroxyacetone, acrylic acid dimer, and 2,3-pentanedione in a yield of less than about 2% from hydroxypropionic acid present in the gaseous mixture. In another embodiment of the present invention, the conditions are sufficient to produce each of acetic acid, pyruvic acid, 1,2-propanediol, hydroxyacetone, acrylic acid dimer, and 2,3-pentanedione in a yield of less than about 0.5%, from hydroxypropionic acid present in the gaseous mixture. In one embodiment of the present invention, the conditions are sufficient to produce acetaldehyde in a yield of less than about 8% from hydroxypropionic acid present in the gaseous mixture. In another embodiment of the present invention, the conditions are sufficient to produce acetaldehyde in a yield of less than about 4% from hydroxypropionic acid present in the gaseous mixture. In another embodiment of the present invention, the conditions are sufficient to produce acetaldehyde in a yield of less than about 3%, from hydroxypropionic acid present in the gaseous mixture. These yields are believed to be, heretofore, unattainably low. Yet, these benefits are indeed achievable as further evidenced in the Examples set out below.

In one embodiment of the present invention, a method of making acrylic acid, acrylic acid derivatives, or mixtures thereof comprises: a) diluting an about 88 wt % lactic acid aqueous solution with water to form an about 20 wt % lactic acid aqueous solution; b) heating the about 20 wt % lactic acid aqueous solution at a temperature from about 95° C. to about 100° C. to hydrolyze oligomers of the lactic acid, producing a monomeric lactic acid solution comprising at least about 95 wt % of the lactic acid in monomeric form based on the total amount of lactic acid, lactic acid derivatives, or mixtures thereof; c) combining the monomeric lactic acid solution with nitrogen to form a liquid/gas blend; d) evaporating the liquid/gas blend in a evaporator with inside surface of borosilicate glass with a residence time of about 0.5 s to about 0.6 s at a temperature between about 300° C. and about 375° C. to produce a gas mixture comprising about 2.5 mol % lactic acid and about 50 mol % water; e) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") in a catalytic reactor with an interior surface of borosilicate glass at a GHSV of about 4,500 h$^{-1}$, at a temperature from about 325° C. to about 400° C. under a total pressure from about 10 barg to about 25 barg producing the acrylic acid; and f) cooling the acrylic acid with a residence time between about 0.1 s and about 10 s.

In one embodiment of the present invention, a method of making acrylic acid is provided. The method comprises contacting: (a) a gas mixture comprising: i) lactic acid, ii) water, and iii) nitrogen, wherein said lactic acid is present in an amount of about 2.5 mol % and wherein said water is present in an amount of about 50 mol % based on the total moles of said gas mixture, with (b) a dehydration catalyst precursor mixture comprising: $(KPO_3)_n$, $BaSO_4$, $Ba_2P_2O_7$, and $SiO_2$; wherein said contacting step of said gas mixture with said dehydration catalyst precursor mixture is performed at a temperature from about 325° C. to about 400° C., at a WHSV between about 0.15 (g of lactic acid/g of catalyst·h) and about 1.0 (g of lactic acid/g of catalyst·h), and at a total pressure between about 10 barg and about 25 barg, in a reactor having an interior surface material selected from the group consisting of amorphous silica and borosilicate glass; whereby acrylic acid is produced as a result of said water and said lactic acid being contacted with said dehydration catalyst precursor mixture.

In another embodiment of the present invention, a method of making acrylic acid, acrylic acid derivatives, or mixtures thereof comprises contacting: a) alkyl lactates or a solution comprising alkyl lactates and a solvent; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said acrylic acid, acrylic acid derivatives, or mixtures thereof is produced as a result of said water vapor and said alkyl lactate being contacted with said dehydration catalyst or said dehydration catalyst precursor mixture. In another embodiment of the present invention, said alkyl lactates are selected from the group consisting of methyl lactate, ethyl lactate, butyl lactate, 2-ethylhexyl lactate, and mixtures thereof. In another embodiment of the present invention, said solvent is selected from the group consisting of water, methanol, ethanol, butanol, 2-ethylhexanol, isobutanol, isooctyl alcohol, and mixtures thereof.

In another embodiment of the present invention, a method of making acrylic acid, acrylic acid derivatives, or mixtures thereof comprises: a) providing alkyl lactates or a solution comprising alkyl lactates and a solvent; b) optionally combining the alkyl lactates or the solution comprising the alkyl lactates and a solvent with an essentially chemically inert gas to form a liquid/gas blend; c) evaporating said alkyl lactates, or said solution comprising alkyl lactates and a solvent, or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce said acrylic acid, acrylic acid derivatives, or mixtures thereof.

A method for dehydrating glycerin to acrolein is provided. The method comprises contacting: (a) glycerin, (b) water vapor, and (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said acrolein is produced as a result of said water vapor and said glycerin being contacted with said dehydration catalyst or said dehydration catalyst precursor mixture.

A method for isomerization of lactic acid, lactic acid derivatives, or mixtures thereof into 3-hydroxypropionic acid, 3-hydroxypropionic acid derivatives, or mixtures thereof is provided. The method comprises contacting: (a) 3-hydroxypropionic acid, 3-hydroxypropionic acid derivatives, or mixtures thereof, (b) water vapor, and (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said 3-hydroxypropionic acid, 3-hydroxypropionic acid derivatives, or mixtures thereof are produced as a result of said water vapor and said lactic acid, lactic acid derivatives, or mixtures thereof being contacted with said dehydration catalyst or said dehydration catalyst precursor mixture.

A method for reduction of hydroxypropionic acid, hydroxypropionic acid derivatives, and mixtures thereof into propionic acid, propionic acid derivatives, 1-propanol, 1-propanol derivatives, or mixtures thereof is provided. The method comprises contacting: (a) hydroxypropionic acid, hydroxypropionic acid derivatives, and mixtures thereof; (b) water vapor, (c) hydrogen gas, and (d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby said propionic acid, propionic acid derivatives, 1-propanol, 1-propanol derivatives, or mixtures thereof are produced as a result of said water vapor, said hydrogen gas, and said hydroxypropionic acid, hydroxypropionic acid derivatives, or mixtures thereof being contacted with said dehydration catalyst or said dehydration catalyst precursor mixture. In another embodiment of the present invention, said dehydration catalyst or said dehydration catalyst precursor mixture further comprises one or more transition metals selected from the groups 8 to 12 of the periodic table. Derivatives of propionic acid can be metal or ammonium salts of propionic acid, alkyl esters of propionic acid, or a mixture thereof. Non limiting examples of metal salts of propionic acid are sodium propionate, potassium propionate, and calcium propionate. Non limiting examples of alkyl esters of propionic acid are methyl propionate, ethyl propionate, butyl propionate, 2-ethylhexyl propionate, or mixtures thereof. A derivative of 1-propanol can be 1-alkyloxypropanol.

A method for dehydrating alcohols to alkenes is provided. The method comprises contacting: (a) one or more aliphatic alcohols, (b) water vapor, and (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more amorphous phosphate salt precursors in said dehydration catalyst or said dehydration catalyst precursor mixture; wherein said contacting step is performed at a temperature equal to or greater than the temperature at the triple point of at least one of said one or more amorphous phosphate salts or said one or more amorphous phosphate salt precursors in said dehydration catalyst or said dehydration catalyst precursor mixture; and whereby one or more alkenes are produced as a result of said water vapor and said one or more aliphatic alcohols being contacted with said dehydration catalyst or said dehydration catalyst precursor mixture. Non limiting examples of alcohols are ethanol, n-propanol, isopropanol, n-butanol, sec-butanol, isobutanol, tert-butanol, pentanol, ethylene glycol, propylene glycol, glycerol, other polyhydric alcohols, and alicyclic alcohols.

V. Examples

Example 1

Potassium phosphate monobasic ($KH_2PO_4$), barium phosphate dibasic ($BaHPO_4$), barium sulfate ($BaSO_4$), and amorphous silicon oxide ($SiO_2$) are combined and ground together using a planetary ball mill to obtain a fine solid. The solid is transferred to a glass beaker and calcined at a temperature between about 450° C. and about 450° C. for 4 h to 12 h. The calcined solid is ground and sieved to obtain a dehydration catalyst precursor mixture with particle size between 106 m and 212 µm. The dehydration catalyst precursor mixture is mainly composed of T-$(KPO_3)_n$, $Ba_2P_2O_7$, $BaSO_4$, and amorphous SiO2.

The dehydration catalyst precursor mixture prepared as described above is tested for the conversion of lactic acid to acrylic acid. A glass-lined stainless steel tube is packed with glass wool at the bottom, followed by dehydration catalyst precursor mixture in the middle and free space at the top. The tube is placed inside an aluminum block and a clam shell furnace in a down-flow arrangement and the bottom of the reactor is connected to a catch tank using fused silica lined stainless steel tubing. The reactor is purged by flowing $N_2$ gas (45 mL/min) at 360 psig (25 barg). Then, the reactor is heated until a final temperature of about 375° C. (tube wall temperature) is reached. A liquid solution of lactic acid in water (20.0 wt %) is fed at the top of the reactor at 0.045 mL/min though polyetheretherketone (PEEK™) tubing using a pump. Before contacting the dehydration catalyst, the gas phase concentrations are: nitrogen: 47.9 mol %; lactic acid: 2.5 mol %; and water: 49.6 mol % and the water partial pressure is 186 psi (12.8 bar). After contacting the dehydration catalyst, the reactor effluent is cooled and the liquid containing acrylic acid is collected in the catch tank. The uncondensed gas effluents are discharged.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, comprising any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid, acrylic acid derivatives, or mixtures thereof comprising contacting the following compositions:
   a) hydroxypropionic acid, hydroxypropionic acid derivatives, or mixtures thereof;
   b) water vapor; and
   c) a dehydration catalyst consisting essentially of one or more amorphous phosphate salts, one or more crystalline phosphate salts, and one or more non-phosphate salts; wherein said one or more crystalline phosphate salts and said one or more non-phosphate salts are substantially chemically inert to said one or more amorphous phosphate salts;
   (a) wherein said one or more amorphous phosphate salts consist essentially of:
   i) one or more monovalent cations, and
   ii) one or more phosphate anions selected from the group represented by empirical formula (I):

$$[H_{2(1-x)}PO_{(4-x)}]^- \qquad (I);$$

wherein x is any real number equal to or greater than 0 and equal to or less than 1; wherein said one or more amorphous phosphate salts are neutrally charged;

or any hydrated form of said one or more amorphous phosphate salts, and mixtures thereof;

(b) wherein said one or more crystalline phosphate salts consist essentially of:

i) one or more polyvalent cations, and
ii) one or more phosphate anions selected from the group represented by molecular formula (II):

(c) $[H_{(f-2g-h)}P_fO_{(4f-g)}]^{(2f+h)-}$         (II);

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged;

(d) or any hydrated form of said one or more crystalline phosphate salts, and mixtures thereof;

(e) wherein said one or more non-phosphate salts consist essentially of:

i) one or more polyvalent cations, and
ii) one or more non-phosphate anions selected from the group represented by molecular formulae (III) and (IV):

(f) $[H_{(a-2b)}S_cO_{(4c-b)}]^{(2c-a)-}$         (III)

(g) $[Ta_{2d}O_{(5d+e)}]^{2e-}$         (IV);

wherein a and b are positive integers or zero; wherein c, d, and e are positive integers; wherein (a−2b) is equal to or greater than zero; wherein (2c−a) is greater than zero; wherein said one or more non-phosphate salts are neutrally charged;

(h) or any hydrated form of said one or more non-phosphate salts, and mixtures thereof;

whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst.

2. The method of claim 1, wherein said hydroxypropionic acid, hydroxypropionic acid derivatives, or mixtures thereof are in the gas phase during said contacting step with said dehydration catalyst.

3. A method of making acrylic acid, acrylic acid derivatives, or mixtures thereof comprising contacting the following compositions under conditions:

a gas mixture comprising:
a) hydroxypropionic acid, hydroxypropionic acid derivatives, or mixtures thereof; and
b) water vapor; with a dehydration catalyst consisting essentially of one or more amorphous phosphate salts, one or more crystalline phosphate salts, and one or more non-phosphate salts; wherein said one or more crystalline phosphate salts and said one or more non-phosphate salts are substantially chemically inert to said one or more amorphous phosphate salts;

(i) wherein said one or more amorphous phosphate salts consist essentially of:

i) one or more monovalent cations, and
ii) one or more phosphate anions selected from the group represented by empirical formula (I):

$[H_{2(1-x)}PO_{(4-x)}]^-$         (I);

wherein x is any real number equal to or greater than 0 and equal to or less than 1;

wherein said one or more amorphous phosphate salts are neutrally charged;

or any hydrated form of said one or more amorphous phosphate salts, and mixtures thereof;

(j) wherein said one or more crystalline phosphate salts consist essentially of:

i) one or more polyvalent cations, and
ii) one or more phosphate anions selected from the group represented by molecular formula (II):

(k) $[H_{(f-2g-h)}PO_{(4f-g)}]^{(2f+h)-}$         (II);

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged;

(l) or any hydrated form of said one or more crystalline phosphate salts, and mixtures thereof;

(m) wherein said one or more non-phosphate salts consist essentially of:

i) one or more polyvalent cations, and
ii) one or more non-phosphate anions selected from the group represented by molecular formulae (III) and (IV):

(n) $[H_{(a-2b)}S_cO_{(4c-b)}]^{(2c-a)-}$         (III)

(o) $[Ta_{2d}O_{(5d+e)}]^{2e-}$         (IV);

wherein a and b are positive integers or zero; wherein c, d, and e are positive integers; wherein (a−2b) is equal to or greater than zero; wherein (2c−a) is greater than zero; wherein said one or more non-phosphate salts are neutrally charged;

(p) or any hydrated form of said one or more non-phosphate salts, and mixtures thereof;

whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst.

4. The method of claim 3, wherein said one or more monovalent cations are selected from the group consisting of $K^+$, $Rb^+$, $Cs^+$, and mixtures thereof.

5. The method of claim 3, wherein at least one of said one or more amorphous phosphate salts consists of two or more different monovalent cations selected from the group consisting of $K^+$, $Rb^+$, and $Cs^+$.

6. A method of making acrylic acid, acrylic acid derivatives, or mixtures thereof comprising contacting the following compositions under conditions including a water partial pressure and a temperature:

a gas mixture comprising:
a) hydroxypropionic acid, hydroxypropionic acid derivatives, or mixtures thereof; and
b) water vapor; with a dehydration catalyst consisting essentially of one or more amorphous phosphate salts, one or more crystalline phosphate salts, and one or more non-phosphate salts; wherein said one or more crystalline phosphate salts and said one or more non-phosphate salts are substantially chemically inert to said one or more amorphous phosphate salts;

(q) wherein said one or more amorphous phosphate salts consist essentially of:
i) one or more monovalent cations selected from the group consisting of K$^+$, Rb$^+$, Cs$^+$, and mixtures thereof; and
ii) one or more phosphate anions selected from the group represented by empirical formula (I):

$$[H_{2(1-x)}PO_{(4-x)}]^-  \quad (I);$$

wherein x is any real number equal to or greater than 0 and equal to or less than 1;
wherein said one or more amorphous phosphate salts are neutrally charged;
or any hydrated form of said one or more amorphous phosphate salts, and mixtures thereof;
(r) wherein said one or more crystalline phosphate salts consist essentially of:
i) one or more polyvalent cations, and
ii) one or more phosphate anions selected from the group represented by molecular formula (II):

$$(s) \; [H_{(f-2g-h)}P_fO_{(4f-g)}]^{(2f+h)-} \quad (II);$$

wherein f is a positive integer; wherein g is a positive integer or zero; wherein h is an integer; wherein (f−2g−h) is equal to or greater than zero; wherein (4f−g) is greater than zero; wherein (2f+h) is greater than zero; wherein (4h/f) is equal to or greater than −2 and equal to or less than 1; wherein said one or more crystalline phosphate salts are neutrally charged;
(t) or any hydrated form of said one or more crystalline phosphate salts, and mixtures thereof;
(u) wherein said one or more non-phosphate salts consist essentially of:
i) one or more polyvalent cations, and
ii) one or more non-phosphate anions selected from the group represented by molecular formulae (III) and (IV):

$$(v) \; [H_{(a-2b)}S_cO_{(4c-b)}]^{(2c-a)-} \quad (III)$$

$$(w) \; [Ta_{2d}O_{(5d+e)}]^{2e-} \quad (IV);$$

wherein a and b are positive integers or zero; wherein c, d, and e are positive integers; wherein (a−2b) is equal to or greater than zero; wherein (2c−a) is greater than zero; wherein said one or more non-phosphate salts are neutrally charged;
(x) or any hydrated form of said one or more non-phosphate salts, and mixtures thereof;
(y) wherein the water partial pressure during said contacting step in said gas mixture is equal to or greater than about 0.8 bar; wherein said contacting step is performed at a temperature equal to or greater than about 250° C.; and
(z) whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst.

7. The method of claim 3, wherein said one or more amorphous phosphate salts are selected from the group represented by empirical formula (Ia):

$$M^I H_{2(1-x)}PO_{(4-x)} \quad (Ia);$$

wherein M$^I$ is a monovalent cation; wherein x is any real number equal to or greater than 0 and equal to or less than 1;
or any hydrated form of said one or more amorphous phosphate salts, and mixtures thereof.

8. The method of claim 7, wherein said one or more amorphous phosphate salts are selected from the group consisting of $KH_{2(1-x)}PO_{(4-x)}$, $RbH_{2(1-x)}PO_{(4-x)}$, $CsH_{2(1-x)}PO_{(4-x)}$, any of their hydrated forms, and mixtures thereof; wherein x is any real number equal to or greater than 0 and equal to or less than 1.

9. The method of claim 3, wherein said one or more amorphous phosphate salts are selected from the group represented by empirical formula (Ib):

$$M^I_w N^I_{(1-w)} H_{2(1-x)}PO_{(4-x)} \quad (Ib);$$

wherein M$^I$ and N$^I$ are essentially two different monovalent cations; wherein x is any real number equal to or greater than 0 and equal to or less than 1; wherein w is any real number greater than 0 and less than 1;
or any hydrated form of said one or more amorphous phosphate salts, and mixtures thereof.

10. The method of claim 9, wherein said one or more amorphous phosphate salts are selected from the group consisting of $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrated forms, and mixtures thereof; wherein x is any real number equal to or greater than 0 and equal to or less than 1; wherein w is any real number greater than 0 and less than 1.

11. The method of claim 3, wherein said one or more polyvalent cations of said one or more crystalline phosphate salts and wherein said one or more polyvalent cations of said one or more non-phosphate salts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof.

12. The method of claim 11, wherein said one or more polyvalent cations of said one or more crystalline phosphate salts and wherein said one or more polyvalent cations of said one or more non-phosphate salts are selected from the group consisting of the cations of the metals Mg, Ca, Sr, Ba, Y, Mn, Al, Er, and mixtures thereof.

13. The method of claim 3, wherein said one or more polyvalent cations of said one or more crystalline phosphate salts and wherein said one or more polyvalent cations of said one or more non-phosphate salts are Ba$^{2+}$.

14. The method of claim 3, wherein said one or more phosphate anions of said one or more crystalline phosphate salts are selected from the group represented by molecular formulae (IIa) to (IIg), and mixtures thereof:

$$(bb) \; [HPO_4]^{2-} \quad (IIa)$$

$$(cc) \; [P_2O_7]^{4-} \quad (IIb)$$

$$(dd) \; [P_3O_{10}]^{5-} \quad (IIc)$$

$$(ee) \; [P_4O_{13}]^{6-} \quad (IId)$$

$$(ff) \; [HP_2O_7]^{3-} \quad (IIe)$$

$$(gg) \; [HPO_4]^{2-} \cdot [H_2PO_4]^- \quad (IIf)$$

$$(hh) \; [P_2O_7]^{4-} \cdot [H_2PO_4]^- \quad (IIg).$$

15. The method of claim 14, wherein said one or more phosphate anions of said one or more crystalline phosphate salts are selected from the group represented by molecular formulae (IIa), (IIb), and mixtures thereof:

$$(ii) \; [HPO_4]^{2-} \quad (IIa)$$

$$(jj) \; [P_2O_7]^{4-} \quad (IIb).$$

16. The method of claim 3, wherein said one or more crystalline phosphate salts are selected from the group consisting of $BeHPO_4$, $MgHPO_4$, $CaHPO_4$, $SrHPO_4$, $BaHPO_4$, $BeNH_4PO_4$, $Be_2P_2O_7$, $Mg_2P_2O_7$, $MgK_2P_2O_7$, $Mg_3K_2(P_2O_7)_2$, $Ca_2P_2O_7$, $CaK_2P_2O_7$, $Ca_3K_2(P_2O_7)_2$, $CasK_2(P_2O_7)_3$, $CaRb_2P_2O_7$, $CaCs_2P_2O_7$, $CaMgP_2O_7$, $Ca_3(NH_4)_2(P_2O_7)_2$, $Ca_5(NH_4)_2(P_2O_7)_3$, $Sr_2P_2O_7$, $SrK_2P_2O_7$, $SrRb_2P_2O_7$, $SrCs_2P_2O_7$, $SrMgP_2O_7$, $Ba_2P_2O_7$, $BaMgP_2O_7$, $BaCaP_2O_7$, $Sc_4(P_2O_7)_3$, $ScKP_2O_7$, $ScRbP_2O_7$, $ScCsP_2O_7$, $YKP_2O_7$, $YRbP_2O_7$, $YCsP_2O_7$, $Ti\ P_2O_7$, $Ti_2Ba(P_2O_7)_2$, $Zr\ P_2O_7$, $ZrMgP_2O_7$, $Hf\ P_2O_7$, $V_4(P_2O_7)_3$, $VKP_2O_7$, $VRbP_2O_7$, $VCsP_2O_7$, $V_2Sr(P_2O_7)_2$, $V_2Ba(P_2O_7)_2$, $Nb_2Mg(P_2O_7)_2$, $Cr_4(P_2O_7)_3$, $CrHP_2O_7$, $CrNH_4P_2O_7$, $CrKP_2O_7$, $CrRbP_2O_7$, $CrCsP_2O_7$, $Cr_2Mg(P_2O_7)_2$, $CrCaP_2O_7$, $Cr_2Ca(P_2O_7)_2$, $Cr_2Sr(P_2O_7)_2$, $CrBaP_2O_7$, $Cr_2Ba(P_2O_7)_2$, $MoP_2O_7$, $MoKP_2O_7$, $MoRbP_2O_7$, $MoCsP_2O_7$, $Mo_2Ba(P_2O_7)_2$, $Mn_2P_2O_7$, $MnHP_2O_7$, $MnK_2P_2O_7$, $MnKP_2O_7$, $2Mn_2P_2O_7Mn_2KP_3O_{10}$, $MnRb_2P_2O_7$, $MnRbP_2O_7$, $MnCsP_2O_7$, $MnCaP_2O_7$, $MnSrP_2O_7$, $MnBaP_2O_7$, $ReP_2O_7$, $AlNH_4P_2O_7$, $AlKP_2O_7$, $AlRbP_2O_7$, $GaNH_4P_2O_7$, $GaKP_2O_7$, $GaRbP_2O_7$, $InKP_2O_7$, $InRbP_2O_7$, $InCsP_2O_7$, $In_2Ca(P_2O_7)_2$, $In_2Sr(P_2O_7)_2$, $In_2Ba(P_2O_7)_2$, $SiP_2O_7$, $GeP_2O_7$, $SnP_2O_7$, $PbP_2O_7$, $Sb^V Sb^{III}(P_2O_7)_2$, $Bi_4(P_2O_7)_3$, $BiHP_2O_7$, $La_4(P_2O_7)_3$, $LaHP_2O_7$, $LaKP_2O_7$, $CeP_2O_7$, $Gd_4(P_2O_7)_3$, $GdKP_2O_7$, $GdRbP_2O_7$, $GdCsP_2O_7$, $TbKP_2O_7$, $TbRbP_2O_7$, $TbCsP_2O_7$, $DyKP_2O_7$, $DyRbP_2O_7$, $DyCsP_2O_7$, $HoKP_2O_7$, $HoRbP_2O_7$, $HoCsP_2O_7$, $ErKP_2O_7$, $ErRbP_2O_7$, $ErCsP_2O_7$, $TmKP_2O_7$, $TmRbP_2O_7$, $TmCsP_2O_7$, $YbHP_2O_7$, $YbKP_2O_7$, $YbRbP_2O_7$, $YbCsP_2O_7$, $LuKP_2O_7$, $LuRbP_2O_7$, $LuCsP_2O_7$, $Be_2RbP_3O_{10}$, $Ca_2KP_3O_{10}$, $Ca_2RbP_3O_{10}$, $Ca_2CsP_3O_{10}$, $Sr_2KP_3O_{10}$, $Sr_2RbP_3O_{10}$, $Sr_2CsP_3O_{10}$, $Ba_2KP_3O_{10}$, $Ba_2RbP_3O_{10}$, $Ba_2CsP_3O_{10}$, $Y_5(P_3O_{10})_3$, $VCsP_3O_{10}$, $CrCs_2P_3O_{10}$, $Cr_3K(P_3O_{10})_2$, $Cr_3Rb(P_3O_{10})_2$, $Cr_3Cs(P_3O_{10})_2$, $MnCs_2P_3O_{10}$, $AlCs_2P_3O_{10}$, $Al_3Cs(P_3O_{10})_2$, $GaCs_2P_3O_{10}$, $In_5(P_3O_{10})_3$, $La_5(P_3O_{10})_3$, $Pr_5(P_3O_{10})_3$, $Nd_5(P_3O_{10})_3$, $Sm_5(P_3O_{10})_3$, $Gd_5(P_3O_{10})_3$, $Er_5(P_3O_{10})_3$, $Yb_5(P_3O_{10})_3$, $Ca_3P_4O_{13}$, $Sr_3P_4O_{13}$, $Ba_3P_4O_{13}$, $Ba_2MgP_4O_{13}$, $Y_2P_4O_{13}$, $Cr_2P_4O_{13}$, $Cr_4(P_2O_7)_3$, $Mn_2P_4O_{13}$, $Gd_2P_4O_{13}$, $Pb_3P_4O_{13}$, $Bi_2P_4O_{13}$, $La_2P_4O_{13}$, any of their hydrated forms, and mixtures thereof.

17. The method of claim 16, wherein said one or more crystalline phosphate salts are selected from the group consisting of $MgHPO_4$, $CaHPO_4$, $SrHPO_4$, $BaHPO_4$, $Mg_2P_2O_7$, $Ca_2P_2O_7$, $Sr_2P_2O_7$, $Ba_2P_2O_7$, $YKP_2O_7$, $Mn_2P_2O_7$, $MnKP_2O_7$, $AlKP_2O_7$, $ErKP_2O_7$, $Ca_3P_4O_{13}$, $Sr_3P_4O_{13}$, $Ba_3P_4O_{13}$, any of their hydrated forms, and mixtures thereof.

18. The method of claim 3, wherein said one or more non-phosphate anions are selected from the group represented by molecular formulae (IIIa) to (IIId), (IVa) to (IVg), and mixtures thereof:

(kk) $[SO_4]^{2-}$ (IIIa)

(ll) $[S_2O_7]^{2-}$ (IIIb)

(mm) $[HSO_4]^{1-}$ (IIIc)

(nn) $[SO_4]^{2-} \cdot [HSO_4]^-$ (IIId)

(oo) $[Ta_2O_6]^{2-}$ (IVa)

(pp) $[Ta_2O_7]^{4-}$ (IVb)

(qq) $[Ta_2O_9]^{8-}$ (IVc)

(rr) $[Ta_2O_{10}]^{10-}$ (IVd)

(ss) $[Ta_2O_{11}]^{12-}$ (IVe)

(tt) $[Ta_4O_{11}]^{2-}$ (IVf)

(uu) $[Ta_4O_{15}]^{10-}$ (IVg).

19. The method of claim 18, wherein said one or more non-phosphate anions are selected from the group represented by molecular formulae (IIIa), (IVa), and mixtures thereof:

(vv) $[SO_4]^{2-}$ (IIIa)

(ww) $[Ta_2O_6]^{2-}$ (IVa).

20. The method of claim 3, wherein said one or more non-phosphate salts are selected from the group consisting of $CaSO_4$, $SrSO_4$, $BaSO_4$, $SrK_2(SO_4)_2$, $SrRb_2(SO_4)_2$, $Ca_2K_2(SO_4)_3$, $Ca_2Rb_2(SO_4)_3$, $Ca_2Cs_2(SO_4)_3$, $CaTa_4O_{11}$, $SrTa_4O_{11}$, $BaTa_4O_{11}$, $MgTa_2O_6$, $CaTa_2O_6$, $SrTa_2O_6$, $BaTa_2O_6$, $Mg_2Ta_2O_7$, $Ca_2Ta_2O_7$, $Sr_2Ta_2O_7$, $SrK_2Ta_2O_7$, $Ba_2Ta_2O_7$, $Ba_3Ta_2O$, $Mg_4Ta_2O_9$, $Ca_4Ta_2O_9$, $Sr_4Ta_2O_9$, $Ba_4Ta_2O_9$, $CasTa_2O_{10}$, $Ca_2KTa_3O_{10}$, $Ca_2RbTa_3O_{10}$, $Ca_2CsTa_3O_{10}$, $Sr_2KTa_3O_{10}$, $Sr_2RbTa_3O_{10}$, $Sr_2CsTa_3O_{10}$, $MgsTa_4O_{15}$, $Sr_5Ta_4O_{15}$, $BasTa_4O_{15}$, $Sr_2KTa_5O_{15}$, $Ba_2KTa_5O_{15}$, $Sr_6Ta_2O_{11}$, $Ba_6Ta_2O_{11}$, any of their hydrated forms, and mixtures thereof.

21. The method of claim 20, wherein said one or more non-phosphate salts are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof.

22. The method of claim 3, wherein said one or more amorphous phosphate salts are selected from the group consisting of $KH_{2(1-x)}PO_{(4-x)}$, $RbH_{2(1-x)}PO_{(4-x)}$, $CsH_{2(1-x)}PO_{(4-x)}$, $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrated forms, and mixtures thereof; wherein x is any real number equal to or greater than 0 and equal to or less than 1 and wherein w is any real number greater than 0 and less than 1;
wherein said one or more crystalline phosphate salts are selected from the group consisting of $Ca_2P_2O_7$, $CaHPO_4$, $Sr_2P_2O_7$, $SrHPO_4$, $Ba_2P_2O_7$, $BaHPO_4$, any of their hydrated forms, and mixtures thereof; and
wherein said one or more non-phosphate salts are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof.

23. The method of claim 22, wherein said one or more amorphous phosphate salts is $KH_{2(1-x)}PO_{(4-x)}$; wherein x is any real number equal to or greater than 0 and equal to or less than 1;
wherein said one or more crystalline phosphate salts is $Ba_2P_2O_7$; and
wherein said one or more non-phosphate salts is $BaSO_4$.

24. The method of claim 3, wherein said dehydration catalyst further consists of silicon oxide ($SiO_2$).

25. The method of claim 24, wherein said silicon oxide is selected from the group consisting of amorphous silica, quartz, tridymite, cristobalite, moganite, coesite, and mixtures thereof.

26. The method of claim 25, wherein said dehydration catalyst consists essentially of $KH_{2(1-x)}PO_{(4-x)}$, $BaSO_4$, $Ba_2P_2O_7$, and amorphous silica; wherein x is any real number equal to or greater than 0 and equal to or less than 1.

27. The method of claim 3, wherein the weight fraction of said one or more amorphous phosphate salts in said dehydration catalyst is between about 0.1 and about 0.8.

28. The method of claim 3, wherein said hydroxypropionic acid, hydroxypropionic acid derivatives, or mixtures thereof are lactic acid, lactic acid derivatives, or mixtures thereof.

* * * * *